US008445500B2

(12) United States Patent
Benko et al.

(10) Patent No.: US 8,445,500 B2
(45) Date of Patent: May 21, 2013

(54) PESTICIDAL COMPOSITIONS

(75) Inventors: Zoltan L. Benko, Indianapolis, IN (US);
Gary D. Crouse, Noblesville, IN (US);
W. Randal Erickson, Carmel, IN (US);
James M. Gifford, Lebanon, IN (US);
Gary D. Gustafson, Zionsville, IN (US);
Nailah Orr, Carmel, IN (US); Gerald B. Watson, Zionsville, IN (US)

(73) Assignee: Dow AgroSciences, LLC., Indianapolis, IN (US)

( * ) Notice: Subject to any disclaimer, the term of this patent is extended or adjusted under 35 U.S.C. 154(b) by 0 days.

(21) Appl. No.: 13/606,723

(22) Filed: Sep. 7, 2012

(65) Prior Publication Data

US 2012/0329821 A1    Dec. 27, 2012

Related U.S. Application Data

(62) Division of application No. 12/210,621, filed on Sep. 15, 2008, now Pat. No. 8,288, 392.

(60) Provisional application No. 60/997,571, filed on Oct. 4, 2007.

(51) Int. Cl.
*A01P 5/00* (2006.01)
*A01P 7/04* (2006.01)
*A01P 7/02* (2006.01)
*A01N 43/40* (2006.01)
*A01N 43/54* (2006.01)

(52) U.S. Cl.
USPC .......................................... 514/256; 705/500

(58) Field of Classification Search .................. None
See application file for complete search history.

(56) References Cited

U.S. PATENT DOCUMENTS 2,893,816 A   7/1959  Sien et al.
2,938,908 A   5/1960  Sien et al.

FOREIGN PATENT DOCUMENTS

AU  A-73642/87    12/1987
DE  3644799 A1    12/1987
DE  19650378 A1   6/1998
EP  0447891       3/1991
JP  61-1665       1/1986
JP  11-269154     10/1999
WO  WO2009/045702 4/2009

OTHER PUBLICATIONS

H. Bredereck, G. Simchen, H. Traut: "Synthesen und Reaktionen von 4-Chlor-5-cyan-pyrimidin. Synthese von 4-Amino- und 4-hydroxy-pyrimidin-aldehyd" Chemische Berichte, vol. 100, No. 11, 1967, pp. 3664-3670.
A. Kirpal, E. Reiter: "Uber einige Dirivate und Oxydationsprodukte von 2- Amno-pyridin." Chemische Berichte, vol. 60, No. 3, 1927, pp. 664-666.
H. Beyer, H-J. Haase, W. Wildgrube: Benzidinartige Umlagerungen in de Pyridinreihe, Chemische Berichte, vol. 90, No. 2, 1957, pp. 247-256.
Database CA [Online] Chemical Abstracts Service, Columbus, Ohio, US; Colonna, Martino et al: "Studies of N-heterocyclic azo coumpounds. I. Action of halo acids on 2-phenylazopyridine" revivide from STN Database accesion No. 1958:1914.
Database CA [Onlilne] Chemical Abstracts Service, Columbus, Ohio, US; Stafford, W.H.et al: "The reduction of azo compounds with hydrazine" retrieved from STN Database accession No. 1957:34856.
Database CA [Online] Chemical Abstracts Service, Columbus, Ohio, US; Ackermann, Martin N. et al: "Tetracarbonylmolybdenum complexes of 2- (phenylhydrazino) pyridine ligands. Correlations of spectroscopic data with pyridyl substituent effects" retrieved from STN Database accession No. 2003-91325.
Database CA [Online] Chemical Abstracts Service, Columbus, OH, US; Kobrakov, K.I. et al: "Halogen-containing pyridines. 7. Synthesis and some conversions of (3,5-dichloro-2-pyridyl) hydrazine" retrieved from STN Database accession No. 2001:95183.
Database CA [Online] Chemical Abstracts Service, Columbus, Ohio, US; Colonna, Martino et al: "Aromatic N-oxides. Action of halogenated acids on N-oxides of 2-phenylazopyridine and 2-phenylazoxypyridine" retrieved from STN database accession No. 1956:56911.
Database CA [Online] Chemical Abstracts Service, Columbus, Ohio, US; Andrisano, Renato et al: "Studies of pyrimidines. VIII. Reactivity of the halogen in 2-substituted 6-methyl-4-chloropyrimidines" retrieved from STN Database accession No. 1952:29668.
Database WPI Week 19867 Thomson Scientific, London, GB; AN 1986-046544 & JP 61 001665 A (Ishihara Sangyo Kaisha Ltd) Jan. 7, 1986.
Lalo, Ulyana; Verkhratsky, Alexei and Pankratov, Yuri. "Invermectin Potentiates ATPInduced Ion Currents in Cortical Neurones: Evidence for Functional Expression of P2X4 receptors?" Neuroscience Letters 421 (2007) 158-162; www.sciencedirect.com.

*Primary Examiner* — Mina Haghighatian
*Assistant Examiner* — Erin Hirt
(74) *Attorney, Agent, or Firm* — Carl D. Corvin

(57) ABSTRACT

The invention disclosed in this document is related to field of pesticides and their use in controlling pests.

26 Claims, No Drawings

PESTICIDAL COMPOSITIONS

This application claims the benefit of U.S. Provisional Application Ser. No. 60/997,571 filed on Oct. 4, 2007. This application also claims the benefit of U.S. patent application Ser. No. 12/210,621 filed on Sep. 15, 2008, now allowed. These applications are hereby incorporated by reference. The invention disclosed in this document is related to field of pesticides and their use in controlling pests.

FIELD OF THE INVENTION

Background of the Invention

Pests cause millions of human deaths around the world each year. Furthermore, there are more than ten thousand species of pests that cause losses in agriculture. These agricultural losses amount to billions of U.S. dollars each year. Termites cause damage to various structures such as homes. These termite damage losses amount to billions of U.S. dollars each year. As final note, many stored food pests eat and adulterate stored food. These stored food losses amount to billions of U.S. dollars each year, but more importantly, deprive people of needed food.

There is an acute need for new pesticides. Insects are developing resistance to pesticides in current use. Hundreds of insect species are resistant to one or more pesticides. The development of resistance to some of the older pesticides, such as DDT, the carbamates, and the organophosphates, is well known. But resistance has even developed to some of the newer pesticides. Therefore, a need exists for new pesticides and particularly for pesticides that have new modes of action.

The examples given for the substituents are (except for halo) non-exhaustive and must not be construed as limiting the invention disclosed in this document.

"alkoxy" means an alkyl further consisting of a carbon-oxygen single bond, for example, methoxy, ethoxy, propoxy, isopropoxy, 1-butoxy, 2-butoxy, isobutoxy, tert-butoxy, pentoxy, 2-methylbutoxy, 1,1-dimethylpropoxy, hexoxy, heptoxy, octoxy, nonoxy, and decoxy.

"alkyl" means an acyclic, saturated, branched or unbranched, substituent consisting of carbon and hydrogen, for example, methyl, ethyl, propyl, isopropyl, 1-butyl, 2-butyl, isobutyl, tert-butyl, pentyl, 2-methylbutyl, 1,1-dimethylpropyl, hexyl, heptyl, octyl, nonyl, and decyl.

"alkylthio" means an alkyl further consisting of a carbon-sulfur single bond, for example meththio and ethylthio.

"aryl" means a cyclic, aromatic substituent consisting of hydrogen and carbon, for example, phenyl, naphthyl, and biphenylyl.

"halo" means fluoro, chloro, bromo, and iodo.

"haloalkoxy" means an alkoxy further consisting of, from one to the maximum possible number of, identical or different, halos, for example, fluoromethoxy, difluoromethoxy, and trifluoromethoxy.

"haloalkyl" means an alkyl further consisting of, from one to the maximum possible number of, identical or different, halos, for example, fluoromethyl, difluoromethyl, trifluoromethyl, 1-fluoromethyl, 2-fluoroethyl, 2,2,2-trifluoroethyl, chloromethyl, trichloromethyl, and 1,1,2,2-tetrafluoroethyl.

DETAILED DESCRIPTION OF THE INVENTION

The pesticidal compositions comprise a compound having the following structure:

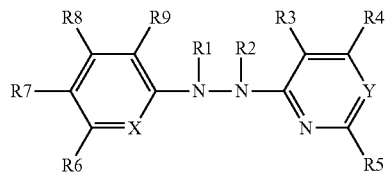

wherein
R1 can be hydro or $C_1$-$C_6$ alkyl;
R2 can be hydro or $C_1$-$C_6$ alkyl;
X can be N or CR11;
Y can be N or CR10;
R3 can be hydro, halo, CN, $NO_2$, $C_1$-$C_6$ alkyl, $C_1$-$C_6$ alkoxy, $C_1$-$C_6$ alkylthio, $C_1$-$C_6$ haloalkyl, $C_1$-$C_6$ haloalkoxy, (C=O)O—$C_1$-$C_6$ alkyl, or N(R12)(R13);
R4 can be hydro, halo, CN, $NO_2$, $C_1$-$C_6$ alkyl, $C_1$-$C_6$ alkoxy, $C_1$-$C_6$ alkylthio, $C_1$-$C_6$ haloalkyl, $C_1$-$C_6$ haloalkoxy, (C=O)O—$C_1$-$C_6$ alkyl, or N(R12)(R13);
R5 can be hydro, halo, CN, $NO_2$, $C_1$-$C_6$ alkyl, $C_1$-$C_6$ alkoxy, $C_1$-$C_6$ alkylthio, $C_1$-$C_6$ haloalkyl, $C_1$-$C_6$ haloalkoxy, (C=O)O—$C_1$-$C_6$ alkyl, or N(R12)(R13);
R6 can be hydro, halo, CN, $NO_2$, $C_1$-$C_6$ alkyl, $C_1$-$C_6$ alkoxy, $C_1$-$C_6$ alkylthio, $C_1$-$C_6$ haloalkyl, $C_1$-$C_6$ haloalkoxy, (C=O)O—$C_1$-$C_6$ alkyl, or N(R12)(R13);
R7 can be hydro, halo, CN, $NO_2$, $C_1$-$C_6$ alkyl, $C_1$-$C_6$ alkoxy, $C_1$-$C_6$ alkylthio, $C_1$-$C_6$ haloalkyl, $C_1$-$C_6$ haloalkoxy, (C=O)O—$C_1$-$C_6$ alkyl, N(R12)(R13), O—S(=O)$_n$—$C_1$-$C_6$ haloalkyl (where n=0-2), S(=O)$_n$—$C_1$-$C_6$ haloalkyl (where n=0-2), or $SO_2$N(R12)(R13);
R8 can be hydro, halo, CN, $NO_2$, $C_1$-$C_6$ alkyl, $C_1$-$C_6$ alkoxy, $C_1$-$C_6$ alkylthio, $C_1$-$C_6$ haloalkyl, $C_1$-$C_6$ haloalkoxy, (C=O)O—$C_1$-$C_6$ alkyl, or N(R12)(R13);
R9 can be hydro, halo, CN, $NO_2$, $C_1$-$C_6$ alkyl, $C_1$-$C_6$ alkoxy, $C_1$-$C_6$ alkylthio, $C_1$-$C_6$ haloalkyl, $C_1$-$C_6$ haloalkoxy, (C=O)O—$C_1$-$C_6$ alkyl, or N(R12)(R13);
R10 can be hydro, halo, CN, $NO_2$, $C_1$-$C_6$ alkyl, $C_1$-$C_6$ alkoxy, $C_1$-$C_6$ alkylthio, $C_1$-$C_6$ haloalkyl, $C_1$-$C_6$ haloalkoxy, (C=O)O—$C_1$-$C_6$ alkyl, or N(R12)(R13);
R11 can be hydro, halo, CN, $NO_2$, $C_1$-$C_6$ alkyl, $C_1$-$C_6$ alkoxy, $C_1$-$C_6$ alkylthio, $C_1$-$C_6$ haloalkyl, $C_1$-$C_6$ haloalkoxy, (C=O)O—$C_1$-$C_6$ alkyl, or N(R12)(R13);
R12 can be hydro or $C_1$-$C_6$ alkyl;
R13 can be hydro or $C_1$-$C_6$ alkyl;
with the following provisos:
(a) that compounds where R1 is H, R2 is H, Y is CR10 and R10 is $CF_3$, X is CR11 and R11 is NO2, R7 is $CF_3$, and R9 is $NO_2$, are excluded;
(b) if Y is N then R5 is not an hydro, halo, or $C_1$-$C_4$ alkyl;
(c) if X is CR11 and one of R9 or R11 is $NO_2$ then Y is not N.

In another embodiment of this invention
R1 can be hydro, methyl, or ethyl;
R2 can be hydro, methyl, or ethyl;
X can be N or CR11;
Y can be N or CR10;
R3 can be hydro, halo, CN, or $NO_2$;
R4 can be hydro, halo, or $C_1$-$C_2$ haloalkyl;
R5 can be hydro, halo, CN, $NH_2$, $C_1$-$C_2$ alkyl, $C_1$-$C_2$ alkylthio, or $C_1$-$C_2$ haloalkyl;
R6 can be hydro;
R7 can be hydro, halo, CN, $NO_2$, $C_1$-$C_6$ alkoxy, $C_1$-$C_6$ haloalkyl, or $SO_2NH_2$;
R8 can be hydro, $NO_2$, or $NH_2$;
R9 can be hydro, halo, or $NO_2$;
R10 can be hydro, halo, CN, $NO_2$, or $C_1$-$C_6$ haloalkyl;

R11 can be hydro, halo, NO$_2$, C$_1$-C$_2$ alkoxy;
with the following provisos:
(a) that compounds where R1 is H, R2 is H, Y is CR10 and R10 is CF$_3$, X is CR11 and R11 is NO$_2$, R7 is CF$_3$, and R9 is NO$_2$, are excluded;
(b) if Y is N then R5 is not an hydro, halo, or C$_1$-C$_4$ alkyl;
(c) if X is CR11 and one of R9 or R11 is NO$_2$ then Y is not N.

In another embodiment of this invention
R1 can be hydro, or methyl;
R2 can be hydro;
X can be N or CR11;
Y can be N or CR10;
R3 can be hydro, Cl, or CN;
R4 can be hydro, or CF$_3$;
R5 can be hydro, CF$_3$, SCH$_3$, Cl, or CN;
R6 can be hydro;
R7 can be hydro, CF$_3$, C$_1$, SO$_2$NH$_2$, NO$_2$, or CN;
R8 can be hydro or NH$_2$;
R9 can be hydro or Cl;
R10 can be hydro, Cl, or CF$_3$;
R11 can be hydro, C$_1$, NO$_2$, OCH$_3$;
with the following provisos:
(b) if Y is N then R5 is not an hydro, or halo;
(c) if X is CR11 and one of R9 or R11 is NO$_2$ then Y is not N.

These provisos are intended to specifically excluded disclosures: JP 61-1665 "Pyridylhydrazine derivatives"; DE 19650378 "Preparation of hydrazino- and azopyrimidines as plant protectants"; and DE 3644799 "Nitrophenylaminopyrimidines, procedure for their preparation, and their use as agrochemical fungicides".

In general, these compounds can be made as follows. A solution of:
1. phenyl-hydrazine or pyridyl-hydrazine, having the desired substituents;
2. 2-halopyridine, 4-halopyrimidine, or 6-halopyrimidine, having the desired substituents; and
3. a solvent such as, for example, ethanol or dimethylformamide;
are mixed together until the reaction is complete. Generally, the temperature is from about 10° C. to about 100° C., but other temperatures may be used. Generally, the pressure is atmospheric, but higher pressures may be used. It is convenient to treat the reaction mixture with a scavenging resin to remove excess hydrazine before removing the solvent under reduced pressure. In the alternative, the reaction mixture can be partitioned between water and dichloromethane, the organic layer can then be dried with sodium sulfate and the solvent can be removed under reduced pressure. When necessary, further purification can be achieved by reversed phase chromatography.

EXAMPLES

The examples are for illustration purposes and are not to be construed as limiting the invention disclosed in this document to only the embodiments disclosed in these examples.

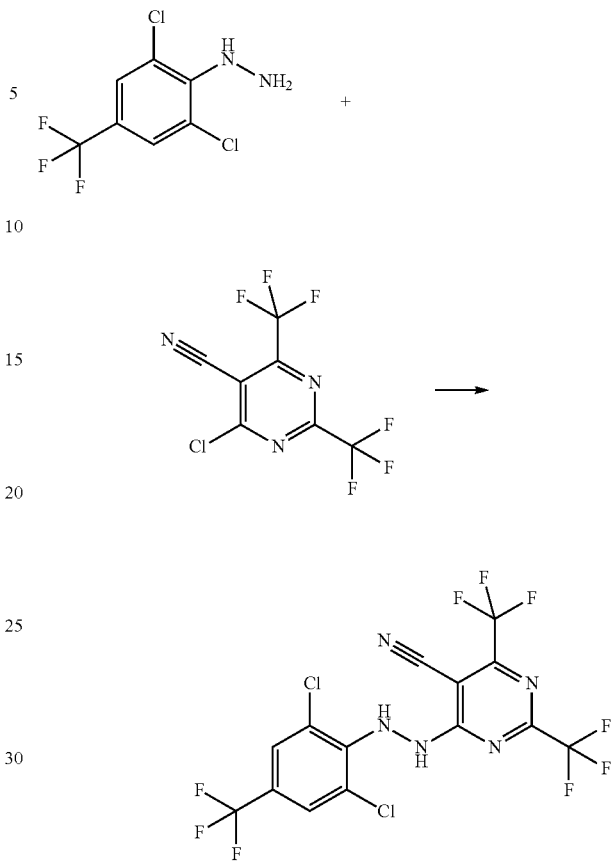

Preparation of 4-[N'-(2,6-dichloro-4-trifluoromethyl-phenyl)-hydrazino]-2,6-bis-trifluoromethyl-pyrimidine-5-carbonitrile A solution of 0.32 g (1.16 mmol) of 4-chloro-2,6-bis-trifluoromethyl-pyrimidine-5-carbonitrile in 5 mL of ethanol was treated with a solution of 0.44 g (1.80 mmol) 2,6-dichloro-4-trifluoromethyl-phenyl)-hydrazine in 2 mL of dichloromethane at room temperature with vigorous stiffing. After 2 hours the reaction mixture was partitioned between water and dichloromethane, the organic layer dried over sodium sulfate and the solvent removed under reduced pressure. The residue was further purified by reversed phase chromatography using an 80% acetonitrile and water mixture containing 0.1% phosphoric acid as eluant to yield 0.42 g (75%) of 4-[N'-(2,6-dichloro-4-trifluoromethyl-phenyl)-hydrazino]-2,6-bis-trifluoromethyl-pyrimidine-5-carbonitrile as an off-white solid: $^1$H NMR (CDCl3) δ 8.38 (bs, 1H), 7.60 (s, 2H), 7.10 (bs) ppm. LCMS: (ESI) m/z 482 (M-1).

Using the general procedure given above and the information given in the preparation the following compounds were produced.

| # | R1 | R2 | R3 | R4 | Y | R10 | R5 | X | R11 | R6 | R7 | R8 | R9 |
|---|----|----|-----|----|---|-----|----|---|-----|----|-----|----|-----|
| 1 | H | H | NO2 | H | C | NO2 | H | C | H | H | NO2 | H | H |
| 2 | H | H | NO2 | H | C | NO2 | H | N | \ | H | NO2 | H | NO2 |

-continued

| # | R1 | R2 | R3 | R4 | Y | R10 | R5 | X | R11 | R6 | R7 | R8 | R9 |
|---|----|----|----|----|---|-----|----|----|-----|----|----|----|----|
| 3 | H | H | H | H | C | H | H | C | Cl | H | H | H | H |
| 4 | H | H | H | H | C | H | H | C | Cl | H | H | NO2 | H |
| 5 | H | H | NO2 | H | C | H | H | N | \ | H | H | H | NO2 |
| 6 | H | H | H | H | C | H | H | C | NO2 | H | CF3 | H | NO2 |
| 7 | H | H | H | H | C | NO2 | NH2 | C | H | H | H | H | H |
| 8 | H | H | CN | H | C | H | H | C | Cl | H | CF3 | H | Cl |
| 9 | H | H | H | CF3 | C | CN | Cl | C | Cl | H | CF3 | H | Cl |
| 10 | H | H | CN | H | C | H | CF3 | C | Cl | H | CF3 | H | Cl |
| 11 | H | H | CN | CF3 | N | \ | CF3 | C | Cl | H | CF3 | H | Cl |
| 12 | H | H | H | CF3 | C | CN | Cl | C | H | H | Cl | H | H |
| 13 | H | H | H | CF3 | C | CN | Cl | C | H | H | OCH3 | H | H |
| 14 | H | H | H | CF3 | N | \ | H | C | Cl | H | CF3 | H | Cl |
| 15 | H | H | CN | CF3 | N | \ | CF3 | C | Cl | H | H | H | Cl |
| 16 | H | H | CN | CF3 | N | \ | CF3 | C | Cl | H | CF3 | H | H |
| 17 | H | H | H | Cl | N | \ | SCH3 | C | Cl | H | CF3 | H | Cl |
| 18 | H | H | H | Cl | N | \ | SCH3 | N | \ | H | Cl | NH2 | Cl |
| 19 | H | H | H | Cl | N | \ | SCH3 | C | H | H | SO2NH2 | H | H |
| 20 | H | H | Cl | H | C | CF3 | H | N | \ | H | Cl | NH2 | Cl |
| 21 | H | H | Cl | H | C | CF3 | H | C | H | H | SO2NH2 | H | H |
| 22 | H | H | H | CF3 | C | H | CF3 | N | \ | H | Cl | NH2 | Cl |
| 23 | H | H | H | CF3 | C | H | CF3 | N | \ | H | Cl | NH2 | Cl |
| 24 | H | H | H | CF3 | C | CN | Cl | N | \ | H | Cl | NH2 | Cl |
| 25 | H | H | H | CF3 | C | CN | Cl | C | H | H | SO2NH2 | H | H |
| 26 | H | H | Cl | H | C | Cl | Cl | N | \ | H | Cl | NH2 | Cl |
| 27 | H | H | Cl | H | C | Cl | Cl | C | H | H | SO2NH2 | H | H |
| 28 | H | H | H | H | C | H | CN | N | \ | H | Cl | NH2 | Cl |
| 29 | CH3 | H | CN | CF3 | N | \ | CF3 | C | H | H | NO2 | H | H |
| 30 | CH3 | H | CN | CF3 | N | \ | CF3 | N | \ | H | CN | H | H |
| 31 | H | H | CN | CF3 | N | \ | CF3 | C | OCH3 | H | H | H | H |
| 32 | CH3 | H | H | Cl | N | \ | SCH3 | C | H | H | NO2 | H | H |
| 33 | CH3 | H | H | Cl | N | \ | SCH3 | N | \ | H | CN | H | H |
| 34 | H | H | H | Cl | N | \ | SCH3 | C | OCH3 | H | H | H | H |
| 35 | CH3 | H | Cl | H | C | CF3 | H | C | H | H | NO2 | H | H |
| 36 | CH3 | H | Cl | H | C | CF3 | H | C | NO2 | H | H | H | H |
| 37 | H | H | Cl | H | C | CF3 | H | C | OCH3 | H | H | H | H |
| 38 | H | H | H | CF3 | C | H | CF3 | C | OCH3 | H | H | H | H |
| 39 | CH3 | H | H | CF3 | C | CN | Cl | C | H | H | NO2 | H | H |
| 40 | CH3 | H | H | CF3 | C | CN | Cl | C | NO2 | H | CF3 | H | H |
| 41 | CH3 | H | H | CF3 | C | CN | Cl | C | NO2 | H | H | H | H |
| 42 | CH3 | H | H | CF3 | C | CN | Cl | N | \ | H | CN | H | H |
| 43 | H | H | H | CF3 | C | CN | Cl | C | OCH3 | H | H | H | H |
| 44 | H | H | Cl | H | C | Cl | Cl | C | OCH3 | H | H | H | H |
| 45 | H | H | H | CF3 | C | H | CH3 | C | NO2 | H | CF3 | H | NO2 |

Insecticidal Test Methods

1. Insecticidal Assay for Beet Armyworm *Spodoptera exigua*:

Objective: To evaluate the insecticidal activity of compounds against *S. exigua* eggs and early instars through contact and ingestion.

Test unit preparation: A robotic system dispenses 150 microliters of freshly prepared artificial lepidopteran diet into each well of a 96-well microtiter plate. The plates are held overnight at 22° C. to allow proper cooling and drying prior to treatment and infestation.

Compound formulation and application: Compounds are formulated in dimethyl sulfoxide at 4-micrograms per microliter. A robotic system automatically dispenses 2 microliters of each of the compound solutions into individual wells of the prepared test units. Each treatment is replicated 6 times. As part of the application process, a 200 ppm concentration of the commonly used synergist, piperonyl butoxide is co-applied to each well to increase the sensitivity of this assay. After application, plates are allowed to dry 5-6 hours in a fume hood. When dry, the plates are covered with a matching lid and held overnight in a sealed container prior to infestation.

Infestation: One day after application, each treated well is infested with 3-5, beet armyworm eggs.

Holding and assessment: Once infested, the plates are covered with a clear plastic lid. The plates are then stacked and held in an incubator at 29° C. After 6 days, each well is examined by means of a microscope for insecticidal effects.

Results: Compounds 8, 9, 11, 15-18, 20-22, 24-26, and 28-30 exhibited significant insecticidal activity, other compounds were either not tested or did not exhibited significant insecticidal activity.

2. Insecticidal Assay for Tobacco Budworm *Heliothis virescens*:

Objective: To evaluate the insecticidal activity of compounds against *H. virescens* eggs and early instars through contact and ingestion.

Test unit preparation: A robotic system dispenses 150 microliters of freshly prepared artificial lepidopteran diet into each well of a 96-well microtiter plate. The plates are held overnight at 22° C. to allow proper cooling and drying prior to treatment and infestation.

Compound formulation and application: Compounds are formulated in dimethyl sulfoxide at 4-micrograms per microliter. A robotic system automatically dispenses 2 microliters of each of the compound solutions into individual wells of the prepared test units. Each treatment is replicated 6 times. As part of the application process, a 200 ppm concentration of the commonly used synergist, piperonyl butoxide is co-applied to each well to increase the sensitivity of this assay. After application, plates are allowed to dry 5-6 hours in a fume hood. When dry, the plates are covered with a matching lid and held overnight in a sealed container prior to infestation.

Infestation: One day after application, each treated well is infested with 3-5, tobacco budworm eggs.

Holding and assessment: Once infested, the plates are covered with a clear plastic lid. The plates are stacked and held in an incubator at 29° C. After 6 days, each well is examined by means of a microscope for insecticidal effects.

Results: Compounds 8, 9, and 11 exhibited significant insecticidal activity, other compounds were either not tested or did not exhibited significant insecticidal activity.

3. Insecticidal Assay for Common Fruit Fly *Drosophila melanogaster* Oregon Wild-Type:

Objective: To evaluate the insecticidal activity of compounds against adult *D. melanogaster* through contact and ingestion.

Test unit preparation: A robotic system dispenses 250 microliters of an agar solution (2% agar in a 10% aqueous sucrose solution) into each well of 96-well microtiter plate where it is allowed to gel. The plates are allowed to cool and dry prior to treatment and infestation.

Compound formulation and application: Compounds are formulated in water:acetone (90:10) diluent at 4-micrograms per microliter. A robotic system automatically dispenses 20 microliters of each the formulated compound solutions into individual wells of the prepared test units. Each treatment is replicated 3 times. After application, test units are placed in a fume hood to dry.

Infesting: One day after treatment, each treated cell is infested with common fruit fly adults.

Holding and assessment: Once infested, the plates are sealed with a clear plastic lid. The plates are then held at 22° C. After 2 days, each well is examined by means of a dissecting microscope for insecticidal effects.

Results: Compounds 11, 15-16, 18, 20, 22, 24, 26, 28-30, 35-37, and 39 exhibited significant insecticidal activity, other compounds were either not tested or did not exhibited significant insecticidal activity.

4. Insecticidal Assay for Yellow Fever Mosquito *Aedes aegypti*:

Objective: To evaluate the insecticidal activity of compounds against *A. aegypti* larvae through contact and ingestion.

Test unit preparation: Empty, 96-well microtiter plates are loaded onto a robotic dispensing system prior to application.

Formulation and application: Compounds are formulated in dimethyl sulfoxide at 4-micrograms per microliter. A robotic system dispenses 1.5 microliters of each formulated experimental solution into each well of an empty, 96-well microtiter plate. Each treatment is replicated 3 times.

Infesting: Subsequent to application, recently hatched, mosquito larvae are suspended in water containing 0.4% mosquito diet (1:3 mix of brewers yeast to liver powder). A robotic system dispenses aliquots of this aqueous solution containing 5-8 first instar mosquitoes into each well of the treated plates.

Holding and assessment: After infestation, the plates are covered with a matching clear plastic lid. Infested plates are stacked and held in an incubator at 22° C. for 72 hours. At assessment, cells are examined by means of a dissecting microscope for insecticidal effects.

Results: Compounds 11, 14, 16, 20, and 30 exhibited significant insecticidal activity, other compounds were either not tested or did not exhibited significant insecticidal activity.

5. Insecticidal Assay for Root-Knot Nematode *Meloidogyne incognita*:

Objective: To evaluate the insecticidal activity of compounds against *M. incognita* through contact and ingestion.

Test unit preparation: Empty, 96-well microtiter plates are loaded onto a robotic dispensing system prior to application.

Formulation and application: A robotic system dispenses 25 microliters of ethanol and 5 micrograms of compound, diluted in dimethyl sulfoxide, into each well of a 96-well flat-bottomed, microtiter plate. There are 3 replicates per treatment. The plates are held 24 hours to allow proper drying prior to further preparation and infestation.

Additional test unit preparation and infestation: After drying, 16 milligrams of media consisting of 2 parts fine soil and 1 part absorbent polymer is added to each well of the treated 96-well plates. Once the media is in place, a 200 microliter aqueous suspension of rootknot nematode eggs is added to each well forming a gelatinous substrate. Into each of these wells are distributed 10 foxtail millet *Seteria italica* seeds. Following this "planting" an identical plate is sealed to the top of the treated plate to allow space for the millet to grow.

Holding and assessment: Once the lids are in place, the plates are held at 27° C. and 75% relative humidity under bright indirect lights. After 7 days, assessment is made by an examination of each well through a dissecting microscope for insecticidal effects.

Results: Compound 11 exhibited significant insecticidal activity, other compounds were either not tested or did not exhibited significant insecticidal activity.

6. Insecticidal Assay for Large Milkweed Bug *Oncopeltus fasciatus*:

Objective: To assess the insecticidal activity of compounds against *O. fasciatus* through contact and ingestion.

Test unit preparation: A robotic system dispenses 100 microliters of freshly prepared artificial diet into each well of a 96-well microtiter plate. The plates are held overnight at 22° C. to allow proper cooling and drying prior to treatment and infestation.

Compound formulation and application: Compounds are formulated in dimethyl sulfoxide at 4-microgram/microliter. A robotic system automatically dispenses 2 microliters of each of the experimental compound solutions into individual wells of the prepared test units. There are 6 replicates per treatment. After application, plates are allowed to dry 5-6 hours in a fume hood. When dry, the plates are covered with a matching lid and held overnight in a sealed container prior to infestation.

Infestation: One day after application, each treated well is infested with 3-5 second instar milkweed bugs.

Holding and assessment: Once infested, the plates are covered with a clear plastic lid. The plates are then stacked and held in an incubator at 29° C. After 6 days, each well is examined by means of a dissecting microscope for insecticidal effect.

Results: Compounds 8 and 11 exhibited significant insecticidal activity, other compounds were either not tested or did not exhibited significant insecticidal activity.

7. Insecticidal Assay for Beet Armyworm *Spodoptera exigua*:

Objective: To assess the insecticidal activity of compounds against *S. exigua*, through contact and ingestion.

Test unit preparation: 8 milliliters of lepidopteran diet is dispensed into one ounce clear plastic portion cups. The diet is allowed to cool before storage or use.

Formulation and application: Eight milligrams of technical compound is dissolved in 20 milliliters of 2:1 acetone:tap water diluent to form a 400 ppm solution. An aliquot of this solution is also used to prepare a 25 parts per million concentration. 250 microliters of each solution is then pipetted onto the surface the diet in each cup. Each treatment is replicated 10 times.

Infestation: Once the treated cups have dried, a single second-instar beet armyworm is placed on the treated diet in each cup.

Holding and assessment: Treated and infested diet cups or are capped and then held in a chamber at 25° C. and 50% relative humidity. 14-hours light:10-hours dark. 5 days after infestation the larvae are assessed for insecticidal effects.

Results: Compounds 9, 11, and 15-16, exhibited significant insecticidal activity, other compounds were either not tested or did not exhibited significant insecticidal activity.

8. Insecticidal Assay for Tobacco Budworm *Heliothis virescens*:

Objective: To assess the insecticidal activity of compounds against *H. virescens* through contact and ingestion.

Test unit preparation: 8 milliliters of lepidopteran diet is dispensed into one ounce clear plastic portion cups. The diet is allowed to cool before storage or use.

Formulation and application: Eight milligrams of technical compound is dissolved in 20 milliliters of 2:1 acetone:tap water diluent to form a 400 ppm solution. An aliquot of this solution is also used to prepare a 25 parts per million concentration. 250 microliters of each solution is then pipetted onto the surface the diet in each cup. Each treatment is replicated 10 times.

Infestation: Once the treated cups have dried, a single second-instar tobacco budworm is placed on the treated diet in each cup.

Holding and assessment: Treated and infested diet cups or are capped and then held in a chamber at 25° C. and 50% relative humidity. 14-hours light:10-hours dark. 5 days after infestation the larvae are assessed for insecticidal effects.

Results: Compounds 9, 11, and 15-16 exhibited significant insecticidal activity, other compounds were either not tested or did not exhibited significant insecticidal activity.

9. Insecticidal Assay for Cabbage Looper *Tricoplusia ni*:

Objective: To assess the insecticidal activity of compounds against *T. ni* through contact and ingestion.

Formulation and application: Eight milligrams of technical compound is dissolved in 20 milliliters of 2:1 acetone:tap water diluent to form a 400 ppm solution. An aliquot of this solution is also used to prepare a 25 parts per million concentration. 3.5 centimeter diameter leaf discs cut from cabbage leaves are dipped into each solution until thoroughly wet. Each treatment is replicated 10 times. After air-drying, the treated discs are placed individually into one-ounce plastic cups.

Infestation: Once the leaf discs have dried, a single second instar cabbage looper is place on the cabbage disc in each cup.

Holding and assessment: Treated and infested cups or are capped and then held in a chamber at 25° C. and 50% relative humidity, 14-hours light:10-hours dark. 5 days after infestation the larvae are assessed for insecticidal effects.

Results: Compounds 9, 11, and 15-16, exhibited significant insecticidal activity, other compounds were either not tested or did not exhibited significant insecticidal activity.

10. Insecticidal Assay for Beet Armyworm *Spodoptera exigua*:

Objective: To assess the insecticidal activity of compounds against *S. exigua* through contact and ingestion.

Test unit preparation: 128 well bioassay trays are prepared by injecting each well with approximately 1 milliliter of prepared lepidopteran diet. Trays are allowed to dry prior to use.

Compound formulation and application: A 1 milligram per milliliter, stock solution is prepared for each compound by adding 2 milliliters of acetone/water diluent (9:1) to a vial containing 2 milligrams of technical compound. From this stock solution, additional doses may be produced through serial dilution. Once the appropriate concentrations have been prepared, 50 microliters of each solution is applied to the surface of the diet in each of 8 wells. Upon completing application, the trays are allowed to dry.

Infestation: Once dry, each well is infested with a single second instar beet armyworm. The infested wells are sealed with self sticking, ventilated plastic covers.

Holding and assessment: After infestation and sealing, the trays are placed in a growth chamber at 25 C and 40% relative humidity. 5 days after infestation the larvae are assessed for insecticidal effects.

Results: Compounds 9, 11, and 15-16, exhibited significant insecticidal activity, other compounds were either not tested or did not exhibited significant insecticidal activity.

11. Insecticidal Assay for Corn Earworm *Helicoverpa zea*:

Objective: To assess the insecticidal activity of compounds against *H. zea*, through contact and ingestion.

Test unit preparation: 128 well bioassay trays are prepared by injecting each well with approximately 1 milliliter of prepared lepidopteran diet. Trays are allowed to dry prior to use.

Compound formulation and application: A 1 milligram per milliliter, stock solution is prepared for each compound by adding 2 milliliters of acetone/water diluent (9:1) to a vial containing 2 milligrams of technical compound. From this stock solution, additional doses may be produced through serial dilution. Once the appropriate concentrations have been prepared, 50 microliters of each solution is applied to the surface of the diet in each of 8 wells. Upon completing application, the trays are allowed to dry.

Infestation: Once dry, each well is infested with a single second instar corn earworm. Infested wells are sealed with self sticking, ventilated plastic covers.

Holding and assessment: After infestation and sealing, the trays are placed in a growth chamber at 25 C and 40% relative humidity. 5 days after infestation the larvae are assessed for insecticidal effects.

Results: Compounds 9, 11 and 15-16 exhibited significant insecticidal activity, other compounds were either not tested or did not exhibited significant insecticidal activity.

12. Insecticidal Assay for German Cockroach *Blattella germanica*:

Objective: Assessment of the insecticidal activity of compounds against *B. germanica* through contact and ingestion.

Test unit preparation: A robotic system dispenses 100 microliters of freshly prepared artificial diet into each well of a 96-well microtiter plate. The plates are held overnight at 22° C. to allow proper cooling and drying prior to treatment and infestation.

Compound formulation and application: Compounds are formulated in dimethyl sulfoxide at 4-microgram/microliter. A robotic system automatically dispenses 2 microliters of each compound solution into individual wells of the prepared test units. Each treatment is replicated 3 times. After application, plates are allowed to dry 5-6 hours in a fume hood. When dry, the plates are covered with a matching lid and held overnight in a sealed container prior to infestation.

Infestation: One day after application, each treated well is infested with 3-5, second instar cockroaches.

Holding and assessment: Once infested, the plates are covered with a clear plastic lid. The plates are stacked and held in an incubator at 29° C. After 6 and 13 days respectively, each well is examined by means of a dissecting microscope for insecticidal effects.

Results: Compound II exhibited significant insecticidal activity, other compounds were either not tested or did not exhibited significant insecticidal activity.

13. Insecticidal Assay for Western Tarnished Plant Bug *Lygus hesperus*:

Objective: Assessment of the insecticidal activity of compounds against *L. hesperus* through egg contact and contact/ingestion activity on emergent nymphs.

Test Unit preparation: Female lygus are allowed to oviposit on snow pea pods, these pods are then placed in plastic Petri dishes.

Formulation and application: Compounds are dissolved in acetone and further dilutes with water containing 0.025% Tween 20. The solutions are sprayed on the Petri dishes and the egg-infested snow pea pods using an airbrush.

Holding and assessment: The Petri dishes are held for 10 days under controlled conditions at which time the emerging nymphs are assessed for insecticidal effects.

Results: Compound 11 exhibited significant insecticidal activity, other compounds were either not tested or did not exhibited significant insecticidal activity.

14. Insecticidal Assay for Cotton Aphid *Aphis gossypii*:

Objective: To assess the insecticidal activity of compounds against *A. gossypii* through contact and ingestion.

Formulation and application: One (1) milligram of each technical synthetic organic compound was dissolved in 1 milliliters of a 90:10 acetone:ethanol solvent. This 1 milliliter of chemical solution was added to 19 milliliters of distilled water containing 0.05% Tween 20 surfactant to produce a 50 parts per million spray solution. A 5 part per million solution was then prepared from the 50 part per million stock.

Test unit preparation and infestation: One week old 'Crookneck' squash plants, trimmed to one cotyledon per plant, are infested with cotton aphids (all life stages). Sections of heavily infested colony squash leaves were placed on the untreated squash cotyledons 16-20 hrs prior to spraying. As the infested sections dried out, the aphids moved to the succulent plant material. Plants are examined to ensure even infestation prior to application.

Application: The plants are sprayed on both sides of all leaves with a hand-held atomizing sprayer until solutions are completely used. Each rate is applied with a sweeping action to 4 plants.

Holding and assessment: The plants are allowed to air dry and are then held for 3 days in a controlled room at 26° C. and 40% relative humidity prior to grading. 3 days after treatment the aphids are assessed for insecticidal effects.

Results: Compounds 9, 11, 14, and 26, exhibited significant insecticidal activity, other compounds were either not tested or did not exhibited significant insecticidal activity.

15. Insecticidal Assay for Green Peach Aphid *Myzus persicae*:

Objective: To assess the insecticidal activity of compounds against *M. persicae* through contact and ingestion.

Formulation and application: One (1) milligram of each technical synthetic organic compound was dissolved in 1 milliliters of a 90:10 acetone:ethanol solvent. This 1 milliliter of chemical solution was added to 19 milliliters of distilled water containing 0.05% Tween 20 surfactant to produce a 50 parts per million spray solution. A 5 part per million solution was then prepared from the 50 part per million stock.

Test unit preparation and infestation: Cabbage seedlings, with 2 to 3 first true leaves emerged (12 days after planting) are culled to 1 plant per 3 inch pot. Treatments consisted of 4 replicates. Four days prior to application, heavily infested colony turnip leaves are shaken above the untreated plants. Shaking dislodges the aphids and they migrate to succulent plant material. Plants are examined to ensure even infestation prior to application.

Application: The plants are sprayed on both sides of all leaves with a hand-held atomizing sprayer until solutions are completely used. Each rate is applied with a sweeping action to 4 plants.

Holding and assessment: The plants are allowed to air dry and are then held for 3 days in a controlled room at 26° C. and 40% relative humidity. 3 days after treatment the aphids are assessed for insecticidal effects.

Results: Compounds 11 and 14 exhibited significant insecticidal activity, other compounds were either not tested or did not exhibited significant insecticidal activity.

Acid & Salt Derivatives, and Solvates

The compounds disclosed in this invention can be in the form of pesticidally acceptable acid addition salts.

By way of non-limiting example, an amine function can form salts with hydrochloric, hydrobromic, sulfuric, phosphoric, acetic, benzoic, citric, malonic, salicylic, malic, fumaric, oxalic, succinic, tartaric, lactic, gluconic, ascorbic, maleic, aspartic, benzenesulfonic, methanesulfonic, ethanesulfonic, hydroxymethanesulfonic, and hydroxyethanesulfonic, acids.

Additionally, by way of non-limiting example, an acid function can form salts including those derived from alkali or alkaline earth metals and those derived from ammonia and amines. Examples of preferred cations include sodium, potassium, magnesium, and aminium cations.

The salts are prepared by contacting the free base form with a sufficient amount of the desired acid to produce a salt. The free base forms may be regenerated by treating the salt with a suitable dilute aqueous base solution such as dilute aqueous NaOH, potassium carbonate, ammonia, and sodium bicarbonate.

As an example, in many cases, a pesticide is modified to a more water soluble form e.g. 2,4-dichlorophenoxy acetic acid dimethyl amine salt is a more water soluble form of 2,4-dichlorophenoxy acetic acid a well known herbicide.

The compounds disclosed in this invention can also form stable complexes with solvent molecules that remain intact after the non-complexed solvent molecules are removed from the compounds. These complexes are often referred to as "solvates".

Stereoisomers

Certain compounds disclosed in this invention can exist as one or more stereoisomers. The various stereoisomers include geometric isomers, diastereomers, and enantiomers. Thus, the compounds disclosed in this invention include racemic mixtures, individual stereoisomers, and optically active mixtures.

It will be appreciated by those skilled in the art that one stereoisomer may be more active than the others. Individual stereoisomers and optically active mixtures may be obtained by selective synthetic procedures, by conventional synthetic procedures using resolved starting materials, or by conventional resolution procedures.

Pests

In another embodiment, the invention disclosed in this document can be used to control pests.

In another embodiment, the invention disclosed in this document can be used to control pests of the Phylum Nematoda.

In another embodiment, the invention disclosed in this document can be used to control pests of the Phylum Arthropoda.

In another embodiment, the invention disclosed in this document can be used to control pests of the Subphylum Chelicerata.

In another embodiment, the invention disclosed in this document can be used to control pests of the Class Arachnida.

In another embodiment, the invention disclosed in this document can be used to control pests of the Subphylum Myriapoda.

In another embodiment, the invention disclosed in this document can be used to control pests of the Class Symphyla.

In another embodiment, the invention disclosed in this document can be used to control pests of the Subphylum Hexapoda.

In another embodiment, the invention disclosed in this document can be used to control pests of the Class Insecta.

In another embodiment, the invention disclosed in this document can be used to control Coleoptera (beetles). A non-exhaustive list of these pests includes, but is not limited to, *Acanthoscelides* spp. (weevils), *Acanthoscelides obtectus* (common bean weevil), *Agrilus planipennis* (emerald ash borer), *Agriotes* spp. (wireworms), *Anoplophora glabripennis* (Asian longhorned beetle), *Anthonomus* spp. (weevils), *Anthonomus grandis* (boll weevil), *Aphidius* spp., *Apion* spp. (weevils), *Apogonia* spp. (grubs), *Ataenius spretulus* (Black Turgrass Ataenius), *Atomaria linearis* (pygmy mangold beetle), *Aulacophore* spp., *Bothynoderes punctiventris* (beet root weevil), *Bruchus* spp. (weevils), *Bruchus pisorum* (pea weevil), *Cacoesia* spp., *Callosobruchus maculatus* (southern cow pea weevil), *Carpophilus hemipteras* (dried fruit beetle), *Cassida vittata, Cerosterna* spp, *Cerotoma* spp. (chrysomeids), *Cerotoma trifurcata* (bean leaf beetle), *Ceutorhynchus* spp. (weevils), *Ceutorhynchus assimilis* (cabbage seedpod weevil), *Ceutorhynchus napi* (cabbage curculio), *Chaetocnema* spp. (chrysomelids), *Colaspis* spp. (soil beetles), *Conoderus scalaris, Conoderus stigmosus, Conotrachelus nenuphar* (plum curculio), *Cotinus nitidis* (Green June beetle), *Crioceris asparagi* (asparagus beetle), *Cryptolestes ferrugineus* (rusty grain beetle), *Cryptolestes pusillus* (flat grain beetle), *Cryptolestes turcicus* (Turkish grain beetle), *Ctenicera* spp. (wireworms), *Curculio* spp. (weevils), *Cyclocephala* spp. (grubs), *Cylindrocpturus adspersus* (sunflower stem weevil), *Deporaus marginatus* (mango leaf-cutting weevil), *Dermestes lardarius* (larder beetle), *Dermestes maculates* (hide beetle), *Diabrotica* spp. (chrysolemids), *Epilachna varivestis* (Mexican bean beetle), *Faustinus cubae, Hylobius pales* (pales weevil), *Hypera* spp. (weevils), *Hypera postica* (alfalfa weevil), *Hyperdoes* spp. (Hyperodes weevil), *Hypothenemus hampei* (coffee berry beetle), *Ips* spp. (engravers), *Lasioderma serricorne* (cigarette beetle), *Leptinotarsa decemlineata* (Colorado potato beetle), *Liogenys fuscus, Liogenys suturalis, Lissorhoptrus oryzophilus* (rice water weevil), *Lyctus* spp. (wood beetles/powder post beetles), *Maecolaspis joliveti, Megascelis* spp., *Melanotus communis, Meligethes* spp., *Meligethes aeneus* (blossom beetle), *Melolontha melolontha* (common European cockchafer), *Oberea brevis, Oberea linearis, Oryctes rhinoceros* (date palm beetle), *Oryzaephilus mercator* (merchant grain beetle), *Oryzaephilus surinamensis* (sawtoothed grain beetle), *Otiorhynchus* spp. (weevils), *Oulema melanopus* (cereal leaf beetle), *Oulema oryzae, Pantomorus* spp. (weevils), *Phyllophaga* spp. (May/June beetle), *Phyllophaga cuyabana, Phyllotreta* spp. (chrysomelids), *Phynchites* spp., *Popillia japonica* (Japanese beetle), *Prostephanus truncates* (larger grain borer), *Rhizopertha dominica* (lesser grain borer), *Rhizotrogus* spp. (Eurpoean chafer), *Rhynchophorus* spp. (weevils), *Scolytus* spp. (wood beetles), *Shenophorus* spp. (Billbug), *Sitona lineatus* (pea leaf weevil), *Sitophilus* spp. (grain weevils), *Sitophilus granaries* (granary weevil), *Sitophilus oryzae* (rice weevil), *Stegobium paniceum* (drugstore beetle), *Tribolium* spp. (flour beetles), *Tribolium castaneum* (red flour beetle), *Tribolium confusum* (confused flour beetle), *Trogoderma variabile* (warehouse beetle), and *Zabrus tenebioides*.

In another embodiment, the invention disclosed in this document can be used to control Dermaptera (earwigs).

In another embodiment, the invention disclosed in this document can be used to control Dictyoptera (cockroaches). A non-exhaustive list of these pests includes, but is not limited to, *Blattella germanica* (German cockroach), *Blatta orientalis* (oriental cockroach), *Parcoblatta pennylvanica, Periplaneta americana* (American cockroach), *Periplaneta australoasiae* (Australian cockroach), *Periplaneta brunnea* (brown cockroach), *Periplaneta fuliginosa* (smokybrown cockroach), *Pyncoselus suninamensis* (Surinam cockroach), and *Supella longipalpa* (brownbanded cockroach).

In another embodiment, the invention disclosed in this document can be used to control Diptera (true flies). A non-exhaustive list of these pests includes, but is not limited to, *Aedes* spp. (mosquitoes), *Agromyza frontella* (alfalfa blotch leafminer), *Agromyza* spp. (leaf miner flies), *Anastrepha* spp. (fruit flies), *Anastrepha suspensa* (Caribbean fruit fly), *Anopheles* spp. (mosquitoes), *Batrocera* spp. (fruit flies), *Bactrocera cucurbitae* (melon fly), *Bactrocera dorsalis* (oriental fruit fly), *Ceratitis* spp. (fruit flies), *Ceratitis capitata* (Mediterranea fruit fly), *Chrysops* spp. (deer flies), *Cochliomyia* spp. (screwworms), *Contarinia* spp. (Gall midges), *Culex* spp. (mosquitoes), *Dasineura* spp. (gall midges), *Dasineura brassicae* (cabbage gall midge), *Delia* spp., *Delia platura* (seedcorn maggot), *Drosophila* spp. (vinegar flies), *Fannia* spp. (filth flies), *Fannia canicularis* (little house fly), *Fannia scalaris* (latrine fly), *Gasterophilus intestinalis* (horse bot fly), *Gracillia perseae, Haematobia irritans* (horn fly), *Hylemyia* spp. (root maggots), *Hypoderma lineatum* (common cattle grub), *Liriomyza* spp. (leafminer flies), *Liriomyza brassica* (serpentine leafminer), *Melophagus ovinus* (sheep ked), *Musca* spp. (muscid flies), *Musca autumnalis* (face fly), *Musca domestica* (house fly), *Oestrus ovis* (sheep bot fly), *Oscinella frit* (frit fly), *Pegomyia betae* (beet leafminer), *Phorbia* spp., *Psila rosae* (carrot rust fly), *Rhagoletis cerasi* (cherry fruit fly), *Rhagoletis pomonella* (apple maggot), *Sitodiplosis mosellana* (orange wheat blossom midge), *Stomoxys calcitrans* (stable fly), *Tabanus* spp. (horse flies), and *Tipula* spp. (crane flies).

In another embodiment, the invention disclosed in this document can be used to control Hemiptera (true bugs). A non-exhaustive list of these pests includes, but is not limited to, *Acrosternum hilare* (green stink bug), *Blissus leucopterus* (chinch bug), *Calocoris norvegicus* (potato mind), *Cimex hemipterus* (tropical bed bug), *Cimex lectularius* (bed bug), *Dagbertus fasciatus, Dichelops furcatus, Dysdercus suturellus* (cotton stainer), *Edessa meditabunda, Eurygaster maura* (cereal bug), *Euschistus heros, Euschistus servus* (brown stink bug), *Helopeltis antonii, Helopeltis theivora* (tea blight plantbug), *Lagynotomus* spp. (stink bugs), *Leptocorisa oratorius, Leptocorisa varicornis, Lygus* spp. (plant bugs), *Lygus hesperus* (western tarnished plant bug), *Maconellicoccus hirsutus, Neurocolpus longirostris, Nezara viridula* (southern green stink bug), *Phytocoris* spp. (plant bugs), *Phytocoris*

*californicus, Phytocoris relativus, Piezodorus guildingi, Poecilocapsus lineatus* (fourlined plant bug), *Psallus vaccinicola, Pseudacysta perseae, Scaptocoris castanea*, and *Triatoma* spp. (bloodsucking conenose bugs/kissing bugs).

In another embodiment, the invention disclosed in this document can be used to control Homoptera (aphids, scales, whiteflies, leafhoppers). A non-exhaustive list of these pests includes, but is not limited to, *Acrythosiphon pisum* (pea aphid), *Adelges* spp. (adelgids), *Aleurodes proletella* (cabbage whitefly), *Aleurodicus disperses, Aleurothrixus floccosus* (woolly whitefly), *Aluacaspis* spp., *Amrasca bigutella bigutella, Aphrophora* spp. (leafhoppers), *Aonidiella aurantii* (California red scale), *Aphis* spp. (aphids), *Aphis gossypii* (cotton aphid), *Aphis pomi* (apple aphid), *Aulacorthum solani* (foxglove aphid), *Bemisia* spp. (whiteflies), *Bemisia argentifolii, Bemisia tabaci* (sweetpotato whitefly), *Brachycolus noxius* (Russian aphid), *Brachycorynella asparagi* (asparagus aphid), *Brevennia rehi, Brevicoryne brassicae* (cabbage aphid), *Ceroplastes* spp. (scales), *Ceroplastes rubens* (red wax scale), *Chionaspis* spp. (scales), *Chrysomphalus* spp. (scales), *Coccus* spp. (scales), *Dysaphis plantaginea* (rosy apple aphid), *Empoasca* spp. (leafhoppers), *Eriosoma lanigerum* (woolly apple aphid), *Icerya purchasi* (cottony cushion scale), *Idioscopus nitidulus* (mango leafhopper), *Laodelphax striatellus* (smaller brown planthopper), *Lepidosaphes* spp., *Macrosiphum* spp., *Macrosiphum euphorbiae* (potato aphid), *Macrosiphum granarium* (English grain aphid), *Macrosiphum rosae* (rose aphid), *Macrosteles quadrilineatus* (aster leafhopper), *Mahanarva frimbiolata, Metopolophium dirhodum* (rose grain aphid), *Mictis longicornis, Myzus persicae* (green peach aphid), *Nephotettix* spp. (leafhoppers), *Nephotettix cinctipes* (green leafhopper), *Nilaparvata lugens* (brown planthopper), *Parlatoria pergandii* (chaff scale), *Parlatoria ziziphi* (ebony scale), *Peregrinus maidis* (corn delphacid), *Philaenus* spp. (spittlebugs), *Phylloxera vitifoliae* (grape phylloxera), *Physokermes piceae* (spruce bud scale), *Planococcus* spp. (mealybugs), *Pseudococcus* spp. (mealybugs), *Pseudococcus brevipes* (pine apple mealybug), *Quadraspidiotus perniciosus* (San Jose scale), *Rhapalosiphum* spp. (aphids), *Rhapalosiphum maida* (corn leaf aphid), *Rhapalosiphum padi* (oat bird-cherry aphid), *Saissetia* spp. (scales), *Saissetia oleae* (black scale), *Schizaphis graminum* (greenbug), *Sitobion avenae* (English grain aphid), *Sogatella furcifera* (white-backed planthopper), *Therioaphis* spp. (aphids), *Toumeyella* spp. (scales), *Toxoptera* spp. (aphids), *Trialeurodes* spp. (whiteflies), *Trialeurodes vaporariorum* (greenhouse whitefly), *Trialeurodes abutiloneus* (bandedwing whitefly), *Unaspis* spp. (scales), *Unaspis yanonensis* (arrowhead scale), and *Zulia entreriana*.

In another embodiment, the invention disclosed in this document can be used to control Hymenoptera (ants, wasps, and bees). A non-exhaustive list of these pests includes, but is not limited to, *Acromyrrmex* spp., *Athalia rosae, Atta* spp. (leafcutting ants), *Camponotus* spp. (carpenter ants), *Diprion* spp. (sawflies), *Formica* spp. (ants), *Iridomyrmex humilis* (Argentine ant), *Monomorium* ssp., *Monomorium minumum* (little black ant), *Monomorium pharaonis* (Pharaoh ant), *Neodiprion* spp. (sawflies), *Pogonomyrmex* spp. (harvester ants), *Polistes* spp. (paper wasps), *Solenopsis* spp. (fire ants), *Tapoinoma sessile* (odorous house ant), *Tetranomorium* spp. (pavement ants), *Vespula* spp. (yellow jackets), and *Xylocopa* spp. (carpenter bees).

In another embodiment, the invention disclosed in this document can be used to control Isoptera (termites). A non-exhaustive list of these pests includes, but is not limited to, *Coptotermes* spp., *Coptotermes curvignathus, Coptotermes frenchii, Coptotermes formosanus* (Formosan subterranean termite), *Cornitermes* spp. (nasute termites), *Cryptotermes* spp. (drywood termites), *Heterotermes* spp. (desert subterranean termites), *Heterotermes aureus, Kalotermes* spp. (drywood termites), *Incistitermes* spp. (drywood termites), *Macrotermes* spp. (fungus growing termites), *Marginitermes* spp. (drywood termites), *Microcerotermes* spp. (harvester termites), *Microtermes obesi, Procornitermes* spp., *Reticulitermes* spp. (subterranean termites), *Reticulitermes banyulensis, Reticulitermes grassei, Reticulitermes flavipes* (eastern subterranean termite), *Reticulitermes hageni, Reticulitermes hesperus* (western subterranean termite), *Reticulitermes santonensis, Reticulitermes speratus, Reticulitermes tibialis, Reticulitermes virginicus, Schedorhinotermes* spp., and *Zootermopsis* spp. (rotten-wood termites).

In another embodiment, the invention disclosed in this document can be used to control Lepidoptera (moths and butterflies). A non-exhaustive list of these pests includes, but is not limited to, *Achoea janata, Adoxophyes* spp., *Adoxophyes orana, Agrotis* spp. (cutworms), *Agrotis ipsilon* (black cutworm), *Alabama argillacea* (cotton leafworm), *Amorbia cuneana, Amyelosis transitella* (navel orangeworm), *Anacamptodes defectaria, Anarsia lineatella* (peach twig borer), *Anomis sabulifera* (jute looper), *Anticarsia gemmatalis* (velvetbean caterpillar), *Archips argyrospila* (fruittree leafroller), *Archips rosana* (rose leaf roller), *Argyrotaenia* spp. (tortricid moths), *Argyrotaenia citrana* (orange tortrix), *Autographa gamma, Bonagota cranaodes, Borbo cinnara* (rice leaf folder), *Bucculatrix thurberiella* (cotton leafperforator), *Caloptilia* spp. (leaf miners), *Capua reticulana, Carposina niponensis* (peach fruit moth), *Chilo* spp., *Chlumetia transversa* (mango shoot borer), *Choristoneura rosaceana* (obliquebanded leafroller), *Chrysodeixis* spp., *Cnaphalocerus medinalis* (grass leafroller), *Colias* spp., *Conpomorpha cramerella, Cossus cossus* (carpenter moth), *Crambus* spp. (Sod webworms), *Cydia funebrana* (plum fruit moth), *Cydia molesta* (oriental fruit moth), *Cydia nignicana* (pea moth), *Cydia pomonella* (codling moth), *Darna diducta, Diaphania* spp. (stem borers), *Diatraea* spp. (stalk borers), *Diatraea saccharalis* (sugarcane borer), *Diatraea graniosella* (southwester corn borer), *Earias* spp. (bollworms), *Earias insulata* (Egyptian bollworm), *Earias vitella* (rough northern bollworm), *Ecdytopopha aurantianum, Elasmopalpus lignosellus* (lesser cornstalk borer), *Epiphysias postruttana* (light brown apple moth), *Ephestia* spp. (flour moths), *Ephestia cautella* (almond moth), *Ephestia elutella* (tobbaco moth), *Ephestia kuehniella* (Mediterranean flour moth), *Epimeces* spp., *Epinotia aporema, Erionota thrax* (banana skipper), *Eupoecilia ambiguella* (grape berry moth), *Euxoa auxiliaris* (army cutworm), *Feltia* spp. (cutworms), *Gortyna* spp. (stemborers), *Grapholita molesta* (oriental fruit moth), *Hedylepta indicata* (bean leaf webber), *Helicoverpa* spp. (noctuid moths), *Helicoverpa armigera* (cotton bollworm), *Helicoverpa zea* (bollworm/corn earworm), *Heliothis* spp. (noctuid moths), *Heliothis virescens* (tobacco budworm), *Hellula undalis* (cabbage webworm), *Indarbela* spp. (root borers), *Keiferia lycopersicella* (tomato pinworm), *Leucinodes orbonalis* (eggplant fruit borer), *Leucoptera malifoliella, Lithocollectis* spp., *Lobesia botrana* (grape fruit moth), *Loxagrotis* spp. (noctuid moths), *Loxagrotis albicosta* (western bean cutworm), *Lymantria dispar* (gypsy moth), *Lyonetia clerkella* (apple leaf miner), *Mahasena corbetti* (oil palm bagworm), *Malacosoma* spp. (tent caterpillars), *Mamestra brassicae* (cabbage armyworm), *Maruca testulalis* (bean pod borer), *Metisa plana* (bagworm), *Mythimna unipuncta* (true armyworm), *Neoleucinodes elegantalis* (small tomato borer), *Nymphula depunctalis* (rice caseworm), *Operophthera brumata* (winter moth), *Ostrinia nubilalis* (European corn borer), *Oxydia vesulia*, *Pandemis cerasana* (common currant tortrix), *Pandemis heparana* (brown apple tortrix), *Papilio demodocus*, *Pectinophora gossypiella* (pink bollworm), *Peridroma* spp. (cutworms), *Peridroma saucia* (variegated cutworm), *Perileucoptera coffeella* (white coffee leafminer), *Phthorimaea operculella* (potato tuber moth), *Phyllocnisitis citrella*, *Phyllonorycter* spp. (leafminers), *Pieris rapae* (imported cabbageworm), *Plathypena scabra*, *Plodia interpunctella* (Indian meal moth), *Plutella xylostella* (diamondback moth), *Polychrosis viteana* (grape berry moth), *Prays endocarpa*, *Prays oleae* (olive moth), *Pseudaletia* spp. (noctuid moths), *Pseudaletia unipunctata* (armyworm), *Pseudoplusia includens* (soybean looper), *Rachiplusia nu*, *Scirpophaga incertulas*, *Sesamia* spp. (stemborers), *Sesamia inferens* (pink rice stem borer), *Sesamia nonagrioides*, *Setora nitens*, *Sitotroga cerealella* (Angoumois grain moth), *Sparganothis pilleriana*, *Spodoptera* spp. (armyworms), *Spodoptera exigua* (beet armyworm), *Spodoptera fugiperda* (fall armyworm), *Spodoptera oridania* (southern armyworm), *Synanthedon* spp. (root borers), *Thecla basilides*, *Thermisia gemmatalis*, *Tineola bisselliella* (webbing clothes moth), *Trichoplusia ni* (cabbage looper), *Tuta absoluta*, *Yponomeuta* spp., *Zeuzera coffeae* (red branch borer), and *Zeuzera pyrina* (leopard moth).

In another embodiment, the invention disclosed in this document can be used to control Mallophaga (chewing lice). A non-exhaustive list of these pests includes, but is not limited to, *Bovicola ovis* (sheep biting louse), *Menacanthus stramineus* (chicken body louse), and *Menopon gallinea* (common hen house).

In another embodiment, the invention disclosed in this document can be used to control Orthoptera (grasshoppers, locusts, and crickets). A non-exhaustive list of these pests includes, but is not limited to, *Anabrus* simplex (Mormon cricket), *Gryllotalpidae* (mole crickets), *Locusta migratoria*, *Melanoplus* spp. (grasshoppers), *Microcentrum retinerve* (angularwinged katydid), *Pterophylla* spp. (kaydids), *chistocerca gregaria*, *Scudderia furcata* (forktailed bush katydid), and *Valanga nigricorni*.

In another embodiment, the invention disclosed in this document can be used to control Phthiraptera (sucking lice). A non-exhaustive list of these pests includes, but is not limited to, *Haematopinus* spp. (cattle and hog lice), *Linognathus ovillus* (sheep louse), *Pediculus humanus capitis* (human body louse), *Pediculus humanus humanus* (human body lice), and *Pthirus pubis* (crab louse), In another embodiment, the invention disclosed in this document can be used to control Siphonaptera (fleas). A non-exhaustive list of these pests includes, but is not limited to, *Ctenocephalides canis* (dog flea), *Ctenocephalides felis* (cat flea), and *Pulex irritans* (human flea).

In another embodiment, the invention disclosed in this document can be used to control Thysanoptera (thrips). A non-exhaustive list of these pests includes, but is not limited to, *Frankliniella fusca* (tobacco thrips), *Frankliniella occidentalis* (western flower thrips), *Frankliniella shultzei Frankliniella williamsi* (corn thrips), *Heliothrips haemorrhaidalis* (greenhouse thrips), *Riphiphorothrips cruentatus*, *Scirtothrips* spp., *Scirtothrips citri* (citrus thrips), *Scirtothrips dorsalis* (yellow tea thrips), *Taeniothrips rhopalantennalis*, and *Thrips* spp.

In another embodiment, the invention disclosed in this document can be used to control Thysanura (bristletails). A non-exhaustive list of these pests includes, but is not limited to, *Lepisma* spp. (silverfish) and *Thermobia* spp. (firebrats).

In another embodiment, the invention disclosed in this document can be used to control Acarina (mites and ticks). A non-exhaustive list of these pests includes, but is not limited to, *Acarapsis woodi* (tracheal mite of honeybees), *Acarus* spp. (food mites), *Acarus siro* (grain mite), *Aceria mangiferae* (mango bud mite), *Aculops* spp., *Aculops lycopersici* (tomato russet mite), *Aculops pelekasi*, *Aculus pelekassi*, *Aculus schlechtendali* (apple rust mite), *Amblyomma americanum* (lone star tick), *Boophilus* spp. (ticks), *Brevipalpus obovatus* (privet mite), *Brevipalpus phoenicis* (red and black flat mite), *Demodex* spp. (mange mites), *Dermacentor* spp. (hard ticks), *Dermacentor variabilis* (american dog tick), *Dermatophagoides pteronyssinus* (house dust mite), *Eotetranycus* spp., *Eotetranychus carpini* (yellow spider mite), *Epitimerus* spp., *Eriophyes* spp., *Ixodes* spp. (ticks), *Metatetranycus* spp., *Notoedres cati*, *Oligonychus* spp., *Oligonychus coffee*, *Oligonychus ilicus* (southern red mite), *Panonychus* spp., *Panonychus citri* (citrus red mite), *Panonychus ulmi* (European red mite), *Phyllocoptruta oleivora* (citrus rust mite), *Polyphagotarsonemun latus* (broad mite), *Rhipicephalus sanguineus* (brown dog tick), *Rhizoglyphus* spp. (bulb mites), *Sarcoptes scabiei* (itch mite), *Tegolophus perseaflorae*, *Tetranychus* spp., *Tetranychus urticae* (twospotted spider mite), and *Varroa destructor* (honey bee mite).

In another embodiment, the invention disclosed in this document can be used to control Nematoda (nematodes). A non-exhaustive list of these pests includes, but is not limited to, *Aphelenchoides* spp. (bud and leaf & pine wood nematodes), *Belonolaimus* spp. (sting nematodes), *Criconemella* spp. (ring nematodes), *Dirofilaria immitis* (dog heartwom), *Ditylenchus* spp. (stem and bulb nematodes), *Heterodera* spp. (cyst nematodes), *Heterodera zeae* (corn cyst nematode), *Hirschmanniella* spp. (root nematodes), *Hoplolaimus* spp. (lance nematodes), *Meloidogyne* spp. (root knot nematodes), *Meloidogyne incognita* (root knot nematode), *Onchocerca volvulus* (hook-tail worm), *Pratylenchus* spp. (lesion nematodes), *Radopholus* spp. (burrowing nematodes), and *Rotylenchus reniformis* (kidney-shaped nematode).

In another embodiment, the invention disclosed in this document can be used to control Symphyla (symphylans). A non-exhaustive list of these pests includes, but is not limited to, *Scutigerella immaculata*.

For more detailed information consult "Handbook of Pest Control—The Behavior, Life Histroy, and Control of Household Pests" by Arnold Mallis, 9th Edition, copyright 2004 by GIE Media Inc.

Mixtures

Some of the pesticides that can be employed beneficially in combination with the invention disclosed in this document include, but are not limited to the following:

1,2 dichloropropane, 1,3 dichloropropene, abamectin, acephate, acequinocyl, acetamiprid, acethion, acetoprole, acrinathrin, acrylonitrile, alanycarb, aldicarb, aldoxycarb, aldrin, allethrin, allosamidin, allyxycarb, alpha cypermethrin, alpha ecdysone, amidithion, amidoflumet, aminocarb, amiton, amitraz, anabasine, arsenous oxide, athidathion, azadirachtin, azamethiphos, azinphos ethyl, azinphos methyl, azobenzene, azocyclotin, azothoate, barium hexafluorosilicate, barthrin, benclothiaz, bendiocarb, benfuracarb, benomyl, benoxafos, bensultap, benzoximate, benzyl benzoate, beta cyfluthrin, beta cypermethrin, bifenazate, bifenthrin, binapacryl, bioallethrin, bioethanomethrin, biopermethrin, bistrifluoron, borax, boric acid, bromfenvinfos, bromo DDT, bromocyclen, bromophos, bromophos ethyl, bromopropylate, bufencarb, buprofezin, butacarb, butathiofos, butocarboxim, butonate, butoxycarboxim, cadusafos, calcium arsenate, calcium polysulfide, camphechlor, carbanolate, carbaryl, carbofuran, carbon disulfide, carbon tetrachloride, carbophenothion, carbosulfan, cartap, chinomethionat, chlorantraniliprole, chlorbenside, chlorbicyclen, chlordane, chlordecone, chlordimeform, chlorethoxyfos, chlorfenapyr, chlorfenethol, chlorfenson, chlorfensulphide, chlorfenvinphos, chlorfluazuron, chlormephos, chlorobenzilate, chloroform, chloromebuform, chloromethiuron, chloropicrin, chloropropylate, chlorphoxim, chlorprazophos, chlorpyrifos, chlorpyrifos methyl, chlorthiophos, chromafenozide, cinerin I, cinerin II, cismethrin, cloethocarb, clofentezine, closantel, clothianidin, copper acetoarsenite, copper arsenate, copper naphthenate, copper oleate, coumaphos, coumithoate, crotamiton, crotoxyphos, cruentaren A &B, crufomate, cryolite, cyanofenphos, cyanophos, cyanthoate, cyclethrin, cycloprothrin, cyenopyrafen, cyflumetofen, cyfluthrin, cyhalothrin, cyhexatin, cypermethrin, cyphenothrin, cyromazine, cythioate, d-limonene, dazomet, DBCP, DCIP, DDT, decarbofuran, deltamethrin, demephion, demephion O, demephion S, demeton, demeton methyl, demeton O, demeton O methyl, demeton S, demeton S methyl, demeton S methylsulphon, diafenthiuron, dialifos, diamidafos, diazinon, dicapthon, dichlofenthion, dichlofluanid, dichlorvos, dicofol, dicresyl, dicrotophos, dicyclanil, dieldrin, dienochlor, diflovidazin, diflubenzuron, dilor, dimefluthrin, dimefox, dimetan, dimethoate, dimethrin, dimethylvinphos, dimetilan, dinex, dinobuton, dinocap, dinocap 4, dinocap 6, dinocton, dinopenton, dinoprop, dinosam, dinosulfon, dinotefuran, dinoterbon, diofenolan, dioxabenzofos, dioxacarb, dioxathion, diphenyl sulfone, disulfuram, disulfoton, dithicrofos, DNOC, dofenapyn, doramectin, ecdysterone, emamectin, EMPC, empenthrin, endosulfan, endothion, endrin, EPN, epofenonane, eprinomectin, esfenvalerate, etaphos, ethiofencarb, ethion, ethiprole, ethoate methyl, ethoprophos, ethyl DDD, ethyl formate, ethylene dibromide, ethylene dichloride, ethylene oxide, etofenprox, etoxazole, etrimfos, EXD, famphur, fenamiphos, fenazaflor, fenazaquin, fenbutatin oxide, fenchlorphos, fenethacarb, fenfluthrin, fenitrothion, fenobucarb, fenothiocarb, fenoxacrim, fenoxycarb, fenpirithrin, fenpropathrin, fenpyroximate, fenson, fensulfothion, fenthion, fenthion ethyl, fentrifanil, fenvalerate, fipronil, flonicamid, fluacrypyrim, fluazuron, flubendiamide, flubenzimine, flucofuron, flucycloxuron, flucythrinate, fluenetil, flufenerim, flufenoxuron, flufenprox, flumethrin, fluorbenside, fluvalinate, fonofos, formetanate, formothion, formparanate, fosmethilan, fospirate, fosthiazate, fosthietan, fosthietan, furathiocarb, furethrin, furfural, gamma cyhalothrin, gamma HCH, halfenprox, halofenozide, HCH, HEOD, heptachlor, heptenophos, heterophos, hexaflumuron, hexythiazox, HHDN, hydramethylnon, hydrogen cyanide, hyprene, hyquincarb, imicyafos, imidacloprid, imiprothrin, indoxacarb, iodomethane, IPSP, isamidofos, isazofos, isobenzan, isocarbophos, isodrin, isofenphos, isoprocarb, isoprothiolane, isothioate, isoxathion, ivermectin jasmolin I, jasmolin II, jodfenphos, juvenile hormone I, juvenile hormone II, juvenile hormone III, kelevan, kinoprene, lambda cyhalothrin, lead arsenate, lepimectin, leptophos, lindane, lirimfos, lufenuron, lythidathion, malathion, malonoben, mazidox, mecarbam, mecarphon, menazon, mephosfolan, mercurous chloride, mesulfen, mesulfenfos, metaflumizone, metam, methacrifos, methamidophos, methidathion, methiocarb, methocrotophos, methomyl, methoprene, methoxychlor, methoxyfenozide, methyl bromide, methyl isothiocyanate, methylchloroform, methylene chloride, metofluthrin, metolcarb, metoxadiazone, mevinphos, mexacarbate, milbemectin, milbemycin oxime, mipafox, mirex, MNAF, monocrotophos, morphothion, moxidectin, naftalofos, naled, naphthalene, nicotine, nifluridide, nikkomycins, nitenpyram, nithiazine, nitrilacarb, novaluron, noviflumuron, omethoate, oxamyl, oxydemeton methyl, oxydeprofos, oxydisulfoton, paradichlorobenzene, parathion, parathion methyl, penfluoron, pentachlorophenol, permethrin, phenkapton, phenothrin, phenthoate, phorate, phosalone, phosfolan, phosmet, phosnichlor, phosphamidon, phosphine, phosphocarb, phoxim, phoxim methyl, pirimetaphos, pirimicarb, pirimiphos ethyl, pirimiphos methyl, potassium arsenite, potassium thiocyanate, pp' DDT, prallethrin, precocene I, precocene II, precocene III, primidophos, proclonol, profenofos, profluthrin, promacyl, promecarb, propaphos, propargite, propetamphos, propoxur, prothidathion, prothiofos, prothoate, protrifenbute, pyraclofos, pyrafluprole, pyrazophos, pyresmethrin, pyrethrin I, pyrethrin II, pyridaben, pyridalyl, pyridaphenthion, pyrifluquinazon, pyrimidifen, pyrimitate, pyriprole, pyriproxyfen, quassia, quinalphos, quinalphos, quinalphos methyl, quinothion, quantifies, rafoxanide, resmethrin, rotenone, ryania, sabadilla, schradan, selamectin, silafluofen, sodium arsenite, sodium fluoride, sodium hexafluorosilicate, sodium thiocyanate, sophamide, spinetoram, spinosad, spirodiclofen, spiromesifen, spirotetramat, sulcofuron, sulfuram, sulfluramid, sulfotep, sulfur, sulfuryl fluoride, sulprofos, tau fluvalinate, tazimcarb, TDE, tebufenozide, tebufenpyrad, tebupirimfos, teflubenzuron, tefluthrin, temephos, TEPP, terallethrin, terbufos, tetrachloroethane, tetrachlorvinphos, tetradifon, tetramethrin, tetranactin, tetrasul, theta cypermethrin, thiacloprid, thiamethoxam, thicrofos, thiocarboxime, thiocyclam, thiodicarb, thiofanox, thiometon, thionazin, thioquinox, thiosultap, thuringiensin, tolfenpyrad, tralomethrin, transfluthrin, transpermethrin, triarathene, triazamate, triazophos, trichlorfon, trichlormetaphos 3, trichloronat, trifenofos, triflumuron, trimethacarb, triprene, vamidothion, vamidothion, vaniliprole, vaniliprole, XMC, xylylcarb, zeta cypermethrin and zolaprofos.

Additionally, any combination of the above pesticides can be used.

The invention disclosed in this document can also be used with herbicides and fungicides, both for reasons of economy and synergy.

The invention disclosed in this document can be used with antimicrobials, bactericides, defoliants, safeners, synergists, algaecides, attractants, desiccants, pheromones, repellants, animal dips, avicides, disinfectants, semiochemicals, and molluscicides (these categories not necessarily mutually exclusive) for reasons of economy, and synergy.

For more information consult "Compendium of Pesticide Common Names" located at http://www.alanwood.net/pesticides/index.html as of the filing date of this document. Also consult "The Pesticide Manual" 14$^{th}$ Edition, edited by C D S Tomlin, copyright 2006 by British Crop Production Council.

Synergistic Mixtures

The invention disclosed in this document can be used with other compounds such as the ones mentioned under the heading "Mixtures" to form synergistic mixtures where the mode of action of the compounds in the mixtures are the same, similar, or different.

Examples of mode of actions include, but are not limited to: acetyl choline esterase inhibitor; sodium channel modulator; chitin biosynthesis inhibitor; GABA-gated chloride channel antagonist; GABA and glutamate-gated chloride channel agonist; acetyl choline receptor agonist; MET I inhibitor; Mg-stimulated ATPase inhibitor; nicotinic acetylcholine receptor; Midgut membrane disrupter; and oxidative phosphorylation disrupter.

Additionally, the following compounds are known as synergists and can be used with the invention disclosed in this document: piperonyl butoxide, piprotal, propyl isome, sesamex, sesamolin, and sulfoxide.

Formulations

A pesticide is rarely suitable for application in its pure form. It is usually necessary to add other substances so that the pesticide can be used at the required concentration and in an appropriate form, permitting ease of application, handling, transportation, storage, and maximum pesticide activity. Thus, pesticides are formulated into, for example, baits, concentrated emulsions, dusts, emulsifiable concentrates, fumigants, gels, granules, microencapsulations, seed treatments, suspension concentrates, suspoemulsions, tablets, water soluble liquids, water dispersible granules or dry flowables, wettable powders, and ultra low volume solutions.

For further information on formulation types see "Catalogue of pesticide formulation types and international coding system" Technical Monograph no 2, $5^{th}$ Edition by CropLife International (2002).

Pesticides are applied most often as aqueous suspensions or emulsions prepared from concentrated formulations of such pesticides. Such water-soluble, water-suspendable, or emulsifiable formulations, are either solids, usually known as wettable powders, or water dispersible granules, or liquids usually known as emulsifiable concentrates, or aqueous suspensions. Wettable powders, which may be compacted to form water dispersible granules, comprise an intimate mixture of the pesticide, a carrier, and surfactants. The concentration of the pesticide is usually from about 10% to about 90% by weight. The carrier is usually chosen from among the attapulgite clays, the montmorillonite clays, the diatomaceous earths, or the purified silicates. Effective surfactants, comprising from about 0.5% to about 10% of the wettable powder, are found among sulfonated lignins, condensed naphthalenesulfonates, naphthalenesulfonates, alkylbenzenesulfonates, alkyl sulfates, and nonionic surfactants such as ethylene oxide adducts of alkyl phenols.

Emulsifiable concentrates of pesticides comprise a convenient concentration of a pesticide, such as from about 50 to about 500 grams per liter of liquid dissolved in a carrier that is either a water miscible solvent or a mixture of water-immiscible organic solvent and emulsifiers. Useful organic solvents include aromatics, especially xylenes and petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are chosen from conventional anionic and nonionic surfactants.

Aqueous suspensions comprise suspensions of water-insoluble pesticides dispersed in an aqueous carrier at a concentration in the range from about 5% to about 50% by weight. Suspensions are prepared by finely grinding the pesticide and vigorously mixing it into a carrier comprised of water and surfactants. Ingredients, such as inorganic salts and synthetic or natural gums, may also be added, to increase the density and viscosity of the aqueous carrier. It is often most effective to grind and mix the pesticide at the same time by preparing the aqueous mixture and homogenizing it in an implement such as a sand mill, ball mill, or piston-type homogenizer.

Pesticides may also be applied as granular compositions that are particularly useful for applications to the soil. Granular compositions usually contain from about 0.5% to about 10% by weight of the pesticide, dispersed in a carrier that comprises clay or a similar substance. Such compositions are usually prepared by dissolving the pesticide in a suitable solvent and applying it to a granular carrier which has been pre-formed to the appropriate particle size, in the range of from about 0.5 to 3 mm. Such compositions may also be formulated by making a dough or paste of the carrier and compound and crushing and drying to obtain the desired granular particle size.

Dusts containing a pesticide are prepared by intimately mixing the pesticide in powdered form with a suitable dusty agricultural carrier, such as kaolin clay, ground volcanic rock, and the like. Dusts can suitably contain from about 1% to about 10% of the pesticide. They can be applied as a seed dressing, or as a foliage application with a dust blower machine.

It is equally practical to apply a pesticide in the form of a solution in an appropriate organic solvent, usually petroleum oil, such as the spray oils, which are widely used in agricultural chemistry.

Pesticides can also be applied in the form of an aerosol composition. In such compositions the pesticide is dissolved or dispersed in a carrier, which is a pressure-generating propellant mixture. The aerosol composition is packaged in a container from which the mixture is dispensed through an atomizing valve.

Pesticide baits are formed when the pesticide is mixed with food or an attractant or both. When the pests eat the bait they also consume the pesticide. Baits may take the form of granules, gels, flowable powders, liquids, or solids. They are use in pest harborages.

Fumigants are pesticides that have a relatively high vapor pressure and hence can exist as a gas in sufficient concentrations to kill pests in soil or enclosed spaces. The toxicity of the fumigant is proportional to its concentration and the exposure time. They are characterized by a good capacity for diffusion and act by penetrating the pest's respiratory system or being absorbed through the pest's cuticle. Fumigants are applied to control stored product pests under gas proof sheets, in gas sealed rooms or buildings or in special chambers.

Pesticides can be microencapsulated by suspending the pesticide particles or droplets in plastic polymers of various types. By altering the chemistry of the polymer or by changing factors in the processing, microcapsules can be formed of various sizes, solubility, wall thicknesses, and degrees of penetrability. These factors govern the speed with which the active ingredient within is released, which, in turn, affects the residual performance, speed of action, and odor of the product.

Oil solution concentrates are made by dissolving pesticide in a solvent that will hold the pesticide in solution. Oil solutions of a pesticide usually provide faster knockdown and kill of pests than other formulations due to the solvents themselves having pesticidal action and the dissolution of the waxy covering of the integument increasing the speed of uptake of the pesticide. Other advantages of oil solutions include better storage stability, better penetration of crevices, and better adhesion to greasy surfaces.

Another embodiment is an oil-in-water emulsion, wherein the emulsion comprises oily globules which are each provided with a lamellar liquid crystal coating and are dispersed in an aqueous phase, wherein each oily globule comprises at least one compound which is agriculturally active, and is individually coated with a monolamellar or oligolamellar layer comprising: (1) at least one non-ionic lipophilic surface-active agent, (2) at least one non-ionic hydrophilic surface-active agent and (3) at least one ionic surface-active agent, wherein the globules having a mean particle diameter of less than 800 nanometers. Further information on the embodiment is disclosed in U.S. patent publication 20070027034 published Feb. 1, 2007, having patent application Ser. No. 11/495,228. For ease of use this embodiment will be referred to as "OIWE".

For further information consult "Insect Pest Management" $2^{nd}$ Edition by D. Dent, copyright CAB International (2000). Additionally, for more detailed information consult "Handbook of Pest Control—The Behavior, Life Histroy, and Control of Household Pests" by Arnold Mallis, $9^{th}$ Edition, copyright 2004 by GIE Media Inc.

Other Formulation Components

Generally, the invention disclosed in this document when used in a formulation, such formulation can also contain other components. These components include, but are not limited to, (this is a non-exhaustive and non-mutually exclusive list) wetters, spreaders, stickers, penetrants, buffers, sequestering agents, drift reduction agents, compatibility agents, antifoam agents, cleaning agents, and emulsifiers. A few components are described forthwith.

A wetting agent is a substance that when added to a liquid increases the spreading or penetration power of the liquid by reducing the interfacial tension between the liquid and the surface on which it is spreading. Wetting agents are used for two main functions in agrochemical formulations: during processing and manufacture to increase the rate of wetting of powders in water to make concentrates for soluble liquids or suspension concentrates; and during mixing of a product with water in a spray tank to reduce the wetting time of wettable powders and to improve the penetration of water into water-dispersible granules. Examples of wetting agents used in wettable powder, suspension concentrate, and water-dispersible granule formulations are: sodium lauryl sulphate; sodium dioctyl sulphosuccinate; alkyl phenol ethoxylates; and aliphatic alcohol ethoxylates.

A dispersing agent is a substance which adsorbs onto the surface of a particles and helps to preserve the state of dispersion of the particles and prevents them from reaggregating. Dispersing agents are added to agrochemical formulations to facilitate dispersion and suspension during manufacture, and to ensure the particles redisperse into water in a spray tank. They are widely used in wettable powders, suspension concentrates and water-dispersible granules. Surfactants that are used as dispersing agents have the ability to adsorb strongly onto a particle surface and provide a charged or steric barrier to reaggregation of particles. The most commonly used surfactants are anionic, non-ionic, or mixtures of the two types. For wettable powder formulations, the most common dispersing agents are sodium lignosulphonates. For suspension concentrates, very good adsorption and stabilization are obtained using polyelectrolytes, such as sodium naphthalene sulphonate formaldehyde condensates. Tristyrylphenol ethoxylate phosphate esters are also used. Non-ionics such as alkylarylethylene oxide condensates and EO-PO block copolymers are sometimes combined with anionics as dispersing agents for suspension concentrates, In recent years, new types of very high molecular weight polymeric surfactants have been developed as dispersing agents. These have very long hydrophobic 'backbones' and a large number of ethylene oxide chains forming the 'teeth' of a 'comb' surfactant. These high molecular weight polymers can give very good long-term stability to suspension concentrates because the hydrophobic backbones have many anchoring points onto the particle surfaces. Examples of dispersing agents used in agrochemical formulations are: sodium lignosulphonates; sodium naphthalene sulphonate formaldehyde condensates; tristyrylphenol ethoxylate phosphate esters; aliphatic alcohol ethoxylates; alky ethoxylates; EO-PO block copolymers; and graft copolymers.

An emulsifying agent is a substance which stabilizes a suspension of droplets of one liquid phase in another liquid phase. Without the emulsifying agent the two liquids would separate into two immiscible liquid phases. The most commonly used emulsifier blends contain alkylphenol or aliphatic alcohol with 12 or more ethylene oxide units and the oil-soluble calcium salt of dodecylbenzene sulphonic acid. A range of hydrophile-lipophile balance ("HLB") values from 8 to 18 will normally provide good stable emulsions. Emulsion stability can sometimes be improved by the addition of a small amount of an EO-PO block copolymer surfactant.

A solubilizing agent is a surfactant which will form micelles in water at concentrations above the critical micelle concentration. The micelles are then able to dissolve or solubilized water-insoluble materials inside the hydrophobic part of the micelle. The type of surfactants usually used for solubilization are non-ionics: sorbitan monooleates; sorbitan monooleate ethoxylates; and methyl oleate esters.

Surfactants are sometimes used, either alone or with other additives such as mineral or vegetable oils as adjuvants to spray-tank mixes to improve the biological performance of the pesticide on the target. The types of surfactants used for bioenhancement depend generally on the nature and mode of action of the pesticide. However, they are often non-ionics such as: alky ethoxylates; linear aliphatic alcohol ethoxylates; aliphatic amine ethoxylates.

A carrier or diluent in an agricultural formulation is a material added to the pesticide to give a product of the required strength. Carriers are usually materials with high absorptive capacities, while diluents are usually materials with low absorptive capacities. Carriers and diluents are used in the formulation of dusts, wettable powders, granules and water-dispersible granules.

Organic solvents are used mainly in the formulation of emulsifiable concentrates, ULV formulations, and to a lesser extent granular formulations. Sometimes mixtures of solvents are used. The first main groups of solvents are aliphatic paraffinic oils such as kerosene or refined paraffins. The second main group and the most common comprises the aromatic solvents such as xylene and higher molecular weight fractions of $C_9$ and $C_{10}$ aromatic solvents. Chlorinated hydrocarbons are useful as cosolvents to prevent crystallization of pesticides when the formulation is emulsified into water. Alcohols are sometimes used as cosolvents to increase solvent power.

Thickeners or gelling agents are used mainly in the formulation of suspension concentrates, emulsions and suspoemulsions to modify the rheology or flow properties of the liquid and to prevent separation and settling of the dispersed particles or droplets. Thickening, gelling, and anti-settling agents generally fall into two categories, namely water-insoluble particulates and water-soluble polymers. It is possible to produce suspension concentrate formulations using clays and silicas. Examples of these types of materials, include, but are not limited to, montmorillonite, e.g. bentonite; magnesium aluminum silicate; and attapulgite. Water-soluble polysaccharides have been used as thickening-gelling agents for many years. The types of polysaccharides most commonly used are natural extracts of seeds and seaweeds or are synthetic derivatives of cellulose. Examples of these types of materials include, but are not limited to, guar gum; locust bean gum; carrageenam; alginates; methyl cellulose; sodium carboxymethyl cellulose (SCMC); hydroxyethyl cellulose (HEC). Other types of anti-settling agents are based on modified starches, polyacrylates, polyvinyl alcohol and polyethylene oxide. Another good anti-settling agent is xanthan gum.

Microorganisms which cause spoilage of formulated products. Therefore preservation agents are used to eliminate or reduce their effect. Examples of such agents include, but are limited to propionic acid and its sodium salt; sorbic acid and its sodium or potassium salts; benzoic acid and its sodium salt; p-hydroxy benzoic acid sodium salt; methyl p-hydroxy benzoate; and 1,2-benzisothiazalin-3-one (BIT).

The presence of surfactants, which lower interfacial tension, often causes water-based formulations to foam during mixing operations in production and in application through a spray tank. In order to reduce the tendency to foam, anti-foam agents are often added either during the production stage or before filling into bottles. Generally, there are two types of anti-foam agents, namely silicones and non-silicones. Silicones are usually aqueous emulsions of dimethyl polysiloxane while the non-silicone anti-foam agents are water-insoluble oils, such as octanol and nonanol, or silica. In both cases, the function of the anti-foam agent is to displace the surfactant from the air-water interface.

For further information see "Chemistry and Technology of Agrochemical Formulations" edited by D. A. Knowles, copyright 1998 by Kluwer Academic Publishers. Also see "Insecticides in Agriculture and Environment—Retrospects and Prospects" by A. S. Perry, I. Yamamoto, I. Ishaaya, and R. Perry, copyright 1998 by Springer-Verlag.

Applications

The actual amount of pesticide to be applied to loci of pests is not critical and can readily be determined by those skilled in the art. In general, concentrations from about 0.01 grams of pesticide per hectare to about 5000 grams of pesticide per hectare are expected to provide good control.

The locus to which a pesticide is applied can be any locus inhabited by an pest, for example, vegetable crops, fruit and nut trees, grape vines, ornamental plants, domesticated animals, the interior or exterior surfaces of buildings, and the soil around buildings.

Generally, with baits, the baits are placed in the ground where, for example, termites can come into contact with the bait. Baits can also be applied to a surface of a building, (horizontal, vertical, or slant, surface) where, for example, ants, termites, cockroaches, and flies, can come into contact with the bait.

Because of the unique ability of the eggs of some pests to resist pesticides repeated applications may be desirable to control newly emerged larvae.

Systemic movement of pesticides in plants may be utilized to control pests on one portion of the plant by applying the pesticides to a different portion of the plant. For example, control of foliar-feeding insects can be controlled by drip irrigation or furrow application, or by treating the seed before planting. Seed treatment can be applied to all types of seeds, including those from which plants genetically transformed to express specialized traits will germinate. Representative examples include those expressing proteins toxic to invertebrate pests, such as *Bacillus thuringiensis* or other insecticidal toxins, those expressing herbicide resistance, such as "Roundup Ready" seed, or those with "stacked" foreign genes expressing insecticidal toxins, herbicide resistance, nutrition-enhancement or any other beneficial traits. Furthermore, such seed treatments with the invention disclosed in this document can further enhance the ability of a plant to better withstand stressful growing conditions. This results in a healthier, more vigorous plant, which can lead to higher yields at harvest time.

The invention disclosed in this document is suitable for controlling endoparasites and ectoparasites in the veterinary medicine sector or in the field of animal keeping. Compounds according to the invention are applied here in a known manner, such as by oral administration in the form of, for example, tablets, capsules, drinks, granules, by dermal application in the form of, for example, dipping, spraying, pouring on, spotting on, and dusting, and by parenteral administration in the form of, for example, an injection.

The invention disclosed in this document can also be employed advantageously in livestock keeping, for example, cattle, sheep, pigs, chickens, and geese. Suitable formulations are administered orally to the animals with the drinking water or feed. The dosages and formulations that are suitable depend on the species.

Before a pesticide can be used or sold commercially, such pesticide undergoes lengthy evaluation processes by various governmental authorities (local, regional, state, national, international). Voluminous data requirements are specified by regulatory authorities and must be addressed through data generation and submission by the product registrant or by another on the product registrant's behalf. These governmental authorities then review such data and if a determination of safety is concluded, provide the potential user or seller with product registration approval. Thereafter, in that locality where the product registration is granted and supported, such user or seller may use or sell such pesticide.

The headings in this document are for convenience only and must not be used to interpret any portion thereof.

What is claimed is:
1. A process to control pests of the Phylum Nematoda, Arthropoda, or both said process comprising applying to a locus a composition having nematodacidal, arthropodacidal, or both, properties said composition comprising a compound having the following structure:

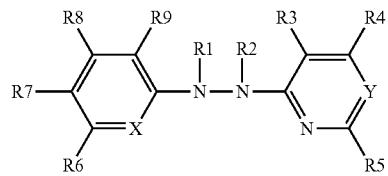

wherein
R1 is H or $C_1$-$C_6$ alkyl;
R2 is H or $C_1$-$C_6$ alkyl;
X is N or CR11;
Y is N or CR10;

R3 is H, halo, CN, $NO_2$, $C_1$-$C_6$ alkyl, $C_1$-$C_6$ alkoxy, $C_1$-$C_6$ alkylthio, $C_1$-$C_6$ haloalkyl, $C_1$-$C_6$ haloalkoxy, (C=O) O—$C_1$-$C_6$ alkyl, or N(R12)(R13);

R4 is H, halo, CN, $NO_2$, $C_1$-$C_6$ alkyl, $C_1$-$C_6$ alkoxy, $C_1$-$C_6$ alkylthio, $C_1$-$C_6$ haloalkyl, $C_1$-$C_6$ haloalkoxy, (C=O) O—$C_1$-$C_6$ alkyl, or N(R12)(R13);

R5 is H, halo, CN, $NO_2$, $C_1$-$C_6$ alkyl, $C_1$-$C_6$ alkoxy, $C_1$-$C_6$ alkylthio, $C_1$-$C_6$ haloalkyl, $C_1$-$C_6$ haloalkoxy, (C=O) O—$C_1$-$C_6$ alkyl, or N(R12)(R13);

R6 is H, halo, CN, $NO_2$, $C_1$-$C_6$ alkyl, $C_1$-$C_6$ alkoxy, $C_1$-$C_6$ alkylthio, $C_1$-$C_6$ haloalkyl, $C_1$-$C_6$ haloalkoxy, (C=O) O—$C_1$-$C_6$ alkyl, or N(R12)(R13);

R7 is H, halo, CN, $NO_2$, $C_1$-$C_6$ alkyl, $C_1$-$C_6$ alkoxy, $C_1$-$C_6$ alkylthio, $C_1$-$C_6$ haloalkyl, $C_1$-$C_6$ haloalkoxy, (C=O) O—$C_1$-$C_6$ alkyl, N(R12)(R13), O—S(=O)$_n$—$C_1$-$C_6$ haloalkyl (where n=0-2), S(=O)$_n$—$C_1$-$C_6$ haloalkyl (where n=0-2), or $SO_2$N(R12)(R13);

R8 is H, halo, CN, $NO_2$, $C_1$-$C_6$ alkyl, $C_1$-$C_6$ alkoxy, $C_1$-$C_6$ alkylthio, $C_1$-$C_6$ haloalkyl, $C_1$-$C_6$ haloalkoxy, (C=O) O—$C_1$-$C_6$ alkyl, or N(R12)(R13);

R9 is H, halo, CN, $NO_2$, $C_1$-$C_6$ alkyl, $C_1$-$C_6$ alkoxy, $C_1$-$C_6$ alkylthio, $C_1$-$C_6$ haloalkyl, $C_1$-$C_6$ haloalkoxy, (C=O) O—$C_1$-$C_6$ alkyl, or N(R12)(R13);

R10 is H, halo, CN, $NO_2$, $C_1$-$C_6$ alkyl, $C_1$-$C_6$ alkoxy, $C_1$-$C_6$ alkylthio, $C_1$-$C_6$ haloalkyl, $C_1$-$C_6$ haloalkoxy, (C=O) O—$C_1$-$C_6$ alkyl, or N(R12)(R13);

R11 is H, halo, CN, $NO_2$, $C_1$-$C_6$ alkyl, $C_1$-$C_6$ alkoxy, $C_1$-$C_6$ alkylthio, $C_1$-$C_6$ haloalkyl, $C_1$-$C_6$ haloalkoxy, (C=O) O—$C_1$-$C_6$ alkyl, or N(R12)(R13);

R12 is H or $C_1$-$C_6$ alkyl;
R13 is H or $C_1$-$C_6$ alkyl;
with the following provisos:
(a) that compounds where R1 is H, R2 is H, Y is CR10 and R10 is $CF_3$, X is CR11 and R11 is NO2, R7 is $CF_3$, and R9 is $NO_2$, are excluded;
(b) if Y is N then R5 is not an H, halo, or $C_1$-$C_4$ alkyl;
(c) if X is CR11 and one of R9 or R11 is $NO_2$ then Y is not N.

2. A process according to claim 1 wherein
R1 is H, methyl, or ethyl;
R2 is H, methyl, or ethyl;
X is N or CR11;
Y is N or CR10;
R3 is H, halo, CN, or $NO_2$;
R4 is H, halo, or $C_1$-$C_2$ haloalkyl;
R5 is H, halo, CN, $NH_2$, $C_1$-$C_2$ alkyl, $C_1$-$C_2$ alkylthio, or $C_1$-$C_2$ haloalkyl;
R6 is H;
R7 is H, halo, CN, $NO_2$, $C_1$-$C_6$ alkoxy, $C_1$-$C_6$ haloalkyl, or $SO_2NH_2$;
R8 is H, $NO_2$, or $NH_2$;
R9 is H, halo, or $NO_2$;
R10 is H, halo, CN, $NO_2$, or $C_1$-$C_6$ haloalkyl;
R11 is H, halo, $NO_2$, $C_1$-$C_2$ alkoxy.

3. A process according to claim 1 wherein
R1 is H, or methyl;
R2 is H;
X is N or CR11;
Y is N or CR10;
R3 is H, Cl, or CN;
R4 is H, or $CF_3$;
R5 is H, $CF_3$, $SCH_3$, Cl, or CN;
R6 is H;
R7 is H, $CF_3$, $C_1$, $SO_2NH_2$, $NO_2$, or CN;
R8 is H or $NH_2$;
R9 is H or Cl;
R10 is H, Cl, or $CF_3$;
R11 is H, $C_1$, $NO_2$, $OCH_3$;
with the following provisos:
(b) if Y is N then R5 is not an H, or halo;
(c) if X is CR11 and one of R9 or R11 is $NO_2$ then Y is not N.

4. A process according to claim 1 wherein said pest is in the Subphylum Chelicerata.

5. A process according to claim 1 wherein said pest is in the Class Arachnida.

6. A process according to claim 1 wherein said pest is in the Subphylum Myriapoda.

7. A process according to claim 1 wherein said pest is in the Class Symphyla.

8. A process according to claim 1 wherein said pest is in the Subphylum Hexapoda.

9. A process according to claim 1 wherein said pest is in Class Insecta.

10. A process according to claim 1 wherein said pest is in Coleoptera.

11. A process according to claim 1 wherein said pest is in Dermaptera.

12. A process according to claim 1 wherein said pest is in Dictyoptera.

13. A process according to claim 1 wherein said pest is in Diptera.

14. A process according to claim 1 wherein said pest is in Hemiptera.

15. A process according to claim 1 wherein said pest is in Hymenoptera.

16. A process according to claim 1 wherein said pest is in Isoptera.

17. A process according to claim 1 wherein said pest is in Lepidoptera.

18. A process according to claim 1 wherein said pest is in Mallophaga.

19. A process according to claim 1 wherein said pest is in Orthoptera.

20. A process according to claim 1 wherein said pest is in Phthiraptera.

21. A process according to claim 1 wherein said pest is in Siphonaptera.

22. A process according to claim 1 wherein said pest is in Thysanoptera.

23. A process according to claim 1 wherein said pest is in Thysanura.

24. A process according to claim 1 wherein said pest is in Acarina.

25. A process according to claim 1 wherein said pest is in Nematoda.

26. A process according to claim 1 wherein said pest is in Symphyla.

* * * * *